(12) United States Patent
Curtis et al.

(10) Patent No.: US 11,060,074 B2
(45) Date of Patent: Jul. 13, 2021

(54) SELF-REGENERATING HYALURONAN POLYMER BRUSHES

(71) Applicant: Georgia Tech Research Corporation, Atlanta, GA (US)

(72) Inventors: Jennifer E. Curtis, Atlanta, GA (US); M. G. Finn, Atlanta, GA (US); Wenbin Wei, Atlanta, GA (US); Jessica Faubel, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 148 days.

(21) Appl. No.: 16/298,820

(22) Filed: Mar. 11, 2019

(65) Prior Publication Data

US 2019/0276807 A1 Sep. 12, 2019

Related U.S. Application Data

(60) Provisional application No. 62/640,985, filed on Mar. 9, 2018.

(51) Int. Cl.
| | |
|---|---|
| *C12N 9/10* | (2006.01) |
| *C12P 19/18* | (2006.01) |
| *C12P 19/04* | (2006.01) |
| *A61L 31/10* | (2006.01) |
| *A01N 25/10* | (2006.01) |
| *A61L 31/14* | (2006.01) |

(Continued)

(52) U.S. Cl.
CPC ........... *C12N 9/1051* (2013.01); *A01N 25/10* (2013.01); *A61K 9/7007* (2013.01);
(Continued)

(58) Field of Classification Search
CPC ........ A61L 27/34; A61L 29/085; A61L 31/10; A61L 2300/236; A61L 2300/252; A61L 2300/41; A61L 2300/412; A61L 2300/426; A61L 27/54; A61L 29/16; A61L 31/16; A61L 27/20; A61L 29/043; A61L 31/042; A61L 31/148; A61L 2300/254; A61L 2300/404; A61L 27/58; A61L 29/148; A61P 35/00; A61P 17/00; A61P 19/02; A61P 11/00; A61P 17/02; A61P 19/00; A61P 19/04; A61P 19/08; A61P 19/10; A61P 1/02; A61P 25/00; A61P 27/02; A61P 29/00; A61P 31/04; A61P 37/02; A61P 37/06; A61P 38/08; A61P 3/10; A61P 43/00; A61P 9/00; A61P 9/10; A61P 31/00; A61P 3/08; A61P 15/00; A61P 17/18; A61Q 19/08; C08L 5/08; A61K 38/00; A61K 47/55; A61K 38/191; A61K 47/69; A61K 47/6957; A61K 47/6937; A61K 31/337; A61K 47/64; A61K 47/6425; A61K 48/00; A61K 48/005; A61K 9/7007; A61K 2039/505; A61K 31/00; A61K 31/185; A61K 31/277; A61K 31/343; A61K 31/4422; A61K 31/47; A61K 31/64; A61K 31/704; A61K 35/17; A61K 38/177; A61K 47/42; A61K 47/542; A61K 47/549; A61K 47/551; A61K 47/60; A61K 47/6935; A61K 48/0066; A61K 49/0032; A61K 49/0056; A61K 49/0093; A61K 9/5169; A61K 2300/00; A61K 38/05; A61K 38/06; A61K 38/07; A61K 31/4172; A61K 8/4946; A61K 8/64; A61K 9/0014; A61K 9/0019; C07K 14/47; C07K 14/525; C07K 14/81; C07K 19/00; C07K 1/36; C07K 14/195; C07K 14/475; C07K 14/00; C07K 14/001; C07K 14/005; C07K 14/4702; C07K 14/5428; C07K 14/5443; C07K 14/605; C07K 14/705; C07K 14/7051; C07K 14/70517; C07K 14/70578; C07K 16/2803; C07K 16/2818; C07K 16/2827; C07K 2317/24; C07K 2317/622; C07K 2317/76; C07K 2318/20; C07K 2319/00; C07K 2319/01; C07K 2319/03; C07K 2319/30; C07K 2319/31; C07K 2319/33; C07K 2319/50; A01N 25/10; A01N 43/16; C07H 21/04; C12N 15/63; C12N 15/79; C12N 9/1051; C12N 11/16; C12N 15/11; C12N 15/111; C12N 15/1131; C12N 15/1132; C12N 2310/14; C12N 2310/20; C12N 2320/11; C12N 2330/10; C12N 2501/125; C12N 2501/145; C12N 2501/22; C12N 2501/2303; C12N 2501/2316; C12N 2740/16022; C12N 2800/80;

(Continued)

(56) References Cited

U.S. PATENT DOCUMENTS

| | | | |
|---|---|---|---|
| 2005/0208095 A1* | 9/2005 | Hunter | ............ A61L 27/54 424/423 |
| 2007/0299043 A1* | 12/2007 | Hunter | ......... A61K 31/553 514/171 |

(Continued)

OTHER PUBLICATIONS

Park et al. "Polymeric self-assembled monolayers derived from surface-active copolymers: a modular approach to functionalized surfaces", Chem. Soc. Rev, 2010, 39 2935-47. (Year: 2010).*

*Primary Examiner* — Deborah K Ware
(74) *Attorney, Agent, or Firm* — Troutman Pepper Hamilton Sanders LLP; Ryan A. Schneider; Dustin B. Weeks

(57) ABSTRACT

The present invention provides polymer brush constructs, for example, surfaces decorated with hyaluronan polymers, and methods of making the same. The constructs are useful as functional materials for numerous applications, e.g., as lubricants, implant coatings, bandages and other uses.

19 Claims, 35 Drawing Sheets

(51) Int. Cl.
    *A61L 31/04*     (2006.01)
    *A61K 9/70*      (2006.01)
    *C12N 11/16*     (2006.01)

(52) U.S. Cl.
    CPC .............. *A61L 31/042* (2013.01); *A61L 31/10* (2013.01); *A61L 31/148* (2013.01); *C12N 11/16* (2013.01); *C12P 19/04* (2013.01); *C12P 19/18* (2013.01); *C12Y 204/01212* (2013.01)

(58) Field of Classification Search
    CPC .......... C12N 5/0647; C12N 9/22; C12N 9/93; C12P 19/04; C12P 19/18; C12Y 204/01212; C12Y 603/04016; Y02A 90/10; Y02A 90/26; B82Y 5/00; C12Q 1/6883; C12Q 1/703; G01N 2333/705; G01N 2500/10; G01N 33/6872
    See application file for complete search history.

(56) References Cited

U.S. PATENT DOCUMENTS

| | | | | |
|---|---|---|---|---|
| 2008/0152640 | A1* | 6/2008 | Prehm | A61K 31/277 424/130.1 |
| 2013/0171461 | A1* | 7/2013 | Dach | C09D 201/02 428/520 |
| 2018/0296343 | A1* | 10/2018 | Wei | B29C 64/386 |

* cited by examiner

A.

B.

A.

B.

A.

B.

C.

A.

B.

A.

B.

A.

B.

C.

D.

A.

B.

C.

D.

SELF-REGENERATING HYALURONAN POLYMER BRUSHES

This application claims the benefit of priority of our prior U.S. provisional application Ser. No. 62/640,985, filed Mar. 9, 2018, the disclosure of which is hereby incorporated by reference in its entirety.

STATEMENT REGARDING FEDERALLY SPONSORED RESEARCH OR DEVELOPMENT

This invention was made with government support under DMR 0955811, DMR 1709897 and PHY 1205878 awarded by the National Science Foundation. The government has certain rights in the invention.

FIELD OF THE INVENTION

The present invention provides polymer brush constructs, for example, surfaces decorated with hyaluronan polymers, and methods of making the same. The constructs are useful as functional materials for numerous applications, e.g., as lubricants, implant coatings, bandages and other uses.

BACKGROUND OF THE INVENTION

The design of functional biomaterials requires exquisite control over interfaces. Integrating physical and chemical features that can be dynamically tuned such as self-healing, stimulus responsiveness, stiffness, crosslinking, or hydrophobicity is a common goal in many modern biomaterials applications (Webber M. J. et al., Supramolecular biomaterials. Nature Materials, 2015, 15:13; Burdick J. A. et al., Moving from static to dynamic complexity in hydrogel design. Nature Communications, 2012, 3: 1269; Rosales A. M. et al., The design of reversible hydrogels to capture extracellular matrix dynamics. Nature Reviews Materials 2016, 1: 15012; Ahn B. K. et al., Surface-initiated self-healing of polymers in aqueous media. Nature Materials, 2014, 13: 867; DeForest C. A. et al., Cytocompatible click-based hydrogels with dynamically tunable properties through orthogonal photoconjugation and photocleavage reactions. Nature Chemistry 2011, 3: 925; Kloxin A. M. et al., Photodegradable Hydrogels for Dynamic Tuning of Physical and Chemical Properties. Science 2009, 324(5923): 59; Mosiewicz K. A. et al., In situ cell manipulation through enzymatic hydrogel photopatterning. Nature Materials 2013, 12: 1072; Zhang S. et al., A pH-responsive supramolecular polymer gel as an enteric elastomer for use in gastric devices. Nature Materials 2015, 14: 1065; Stuart M. A. C. et al., Emerging applications of stimuli-responsive polymer materials. Nature Materials 2010, 9: 101). One popular strategy to engineer such sophisticated biointerfaces is the polymer brush (Krishnamoorthy M. et al., Surface-Initiated Polymer Brushes in the Biomedical Field: Applications in Membrane Science, Biosensing, Cell Culture, Regenerative Medicine and Antibacterial Coatings. Chemical Reviews 2014, 114(21): 10976-11026). Polymer brushes have been used to optimize a range of applications including sensors (Tam T. K. et al., Polymer Brush-Modified Electrode with Switchable and Tunable Redox Activity for Bioelectronic Applications. The Journal of Physical Chemistry C 2008, 112(22): 8438-8445), anti-biofouling coatings (Gunkel G. et al., Effect of Polymer Brush Architecture on Antibiofouling Properties. Biomacromolecules 2011, 12(11): 4169-4172; Nejadnik M. R. et al., Bacterial adhesion and growth on a polymer brush-coating. Biomaterials 2008, 29(30): 4117-4121; Ma H. et al., "Non-Fouling" Oligo(ethylene glycol)-Functionalized Polymer Brushes Synthesized by Surface-Initiated Atom Transfer Radical Polymerization. Advanced Materials 2004, 16(4): 338-341), protein separations (Nagase K. et al., Interfacial Property Modulation of Thermoresponsive Polymer Brush Surfaces and Their Interaction with Biomolecules. Langmuir 2007, 23(18): 9409-9415), drug delivery (Sato A. et al., Polymer brush-stabilized polyplex for a siRNA carrier with long circulatory half-life. Journal of Controlled Release 2007, 122(3): 209-216), tissue engineering (Mizutani A. et al., Preparation of thermoresponsive polymer brush surfaces and their interaction with cells. Biomaterials 2008, 29(13): 2073-2081; Raynor J. E., et al., Polymer brushes and self-assembled monolayers: Versatile platforms to control cell adhesion to biomaterials (Review). Biointerphases 2009, 4(2): FA3-FA16) and implants (Gao G. et al., The biocompatibility and biofilm resistance of implant coatings based on hydrophilic polymer brushes conjugated with antimicrobial peptides. Biomaterials 2011, 32(16): 3899-3909; Busscher H. J., et al. Biofilm Formation on Dental Restorative and Implant Materials. Journal of Dental Research 2010, 89(7): 657-665). The brushes used in these applications are typically high density, and therefore require assembly using a grafting-from strategy rather than a grafting-to approach. This constraint is unfortunate since natural biopolymers are often desirable for biomaterials applications, yet few methodologies exist for the synthetic catalysis of biopolymers from surfaces. Further, many synthetic polymer brushes carry the disadvantage that they cannot be dynamically grown in vivo or regenerated after wear.

The biopolymer hyaluronan (HA, also called hyaluronic acid) is widely used in an array of biomedical and clinical applications (Burdick J. A. et al., Hyaluronic Acid Hydrogels for Biomedical Applications. Advanced Materials 2011, 23(12): H41-H56; Highley C. B., et al., Recent advances in hyaluronic acid hydrogels for biomedical applications. Current Opinion in Biotechnology 2016, 40: 35-40). Ubiquitous throughout human tissues and fluids, hyaluronan is a non-immunogenic polysaccharide comprised of alternating N-acetyl-D-glucosamine and D-glucuronic acid (Fraser J. R. E. et al., Hyaluronan: its nature, distribution, functions and turnover. Journal of Internal Medicine 2003, 242(1): 27-33; Toole B. P. Hyaluronan: from extracellular glue to pericellular cue. Nature Reviews Cancer 2004, 4: 528). It is essential for a multitude of cellular and tissue functions. The role of hyaluronan in the body depends on its size, which can range from a few oligosaccharides (1 disaccharide is 400 Da and corresponds to ~1 nm) to up to at least 25,000 disaccharide units (25 µm, 10 MDa). Hyaluronan is a common component in biomaterials, cosmetics and therapeutics due to its biocompatibility, its ease of chemical modification, its hydrophilic properties, and its large size, which when combined with crosslinking endows valuable viscoelastic properties and the capacity to form extremely hydrated matrices (Zheng Shu X. et al., In situ crosslinkable hyaluronan hydrogels for tissue engineering. Biomaterials 2004, 25(7): 1339-1348; Masters K. S. et al., Crosslinked hyaluronan scaffolds as a biologically active carrier for valvular interstitial cells. Biomaterials 2005, 26(15): 2517-2525).

Man-made hyaluronan polymer brushes are rare and limited by a grafting-to approach (Attili S. et al., Films of End-Grafted Hyaluronan Are a Prototype of a Brush of a Strongly Charged, Semiflexible Polyelectrolyte with Intrinsic Excluded Volume. Biomacromolecules 2012, 13(5): 1466-1477; Richter R. P., et al., Membrane-Grafted Hyaluronan Films: A Well-Defined Model System of Glycoconjugate Cell Coats. Journal of the American Chemical Society 2007, 129(17): 5306-5307). Yet nature generates hyaluronan polymer brush-like structures in the cell glycocalyx (Evanko S. P. et al., Hyaluronan-dependent pericellular matrix. Advanced Drug Delivery Reviews 2007, 59(13): 1351-1365). In organisms ranging from algae to bacteria to vertebrates, hyaluronan is assembled and retained at the cell surface by the enzyme hyaluronan synthase (HA synthase) (Weigel P. H. et al., Hyaluronan Synthases: A Decade-plus of Novel Glycosyltransferases. Journal of Biological Chemistry 2007, 282(51): 36777-36781). This transmembrane protein manages the dual tasks of polymerizing as well as translocating hyaluronan across the cell membrane at ~1 nm/s into the extracellular space (Baggenstoss B. A. et al., Size exclusion chromatography-multiangle laser light scattering analysis of hyaluronan size distributions made by membrane-bound hyaluronan synthase. Analytical Biochemistry 2006, 352(2): 243-251; Weigel P. H. et al., Hyaluronan Synthases. Journal of Biological Chemistry 1997, 272(22): 13997-14000). Hyaluronan synthase, equipped with two glycotransferase sites, utilizes the nucleotide sugar substrates uridine diphosphate glucuronate (UDP-GlcUA) and Uridine diphosphate N-acetylglucosamine (UDP-GlcNAc) in the presence of Mg' to polymerize the hyaluronan. The final hyaluronan product often remains bound to the hyaluronan synthase even after synthesis stops. Although nature's approach has many advantages, it has been difficult to leverage nature's hyaluronan biosynthesis in a feasible way.

Thus, new or improved polymer brushes are continually needed that are versatile, can grow to form ultra-thick, dense materials, whose biocompatibility and possibility for regeneration can be used to control dynamic biointerfaces. The compositions and methods described here are directed to these and other ends.

SUMMARY OF THE INVENTION

The present invention provides polymer brush compositions and methods of making them and using them as functional materials. In particular, Applicants have leveraged the capacity of engineered bacteria to express high densities of hyaluronan synthase in their membranes as well as the ability of hyaluronan synthase to generate extraordinarily long polymers (DeAngelis P. L. et al., Molecular cloning, identification, and sequence of the hyaluronan synthase gene from group A *Streptococcus pyogenes*. Journal of Biological Chemistry 1993, 268(26): 19181-19184; Kumari K. et al., Molecular Cloning, Expression, and Characterization of the Authentic Hyaluronan Synthase from Group C *Streptococcus equisimilis*. Journal of Biological Chemistry 1997, 272(51): 32539-32546) using a new methodology involving the immobilization of and synthase-rich bacterial membrane fragments on interfaces. The present invention provides tunable, regenerative, giant hyaluronan brushes driven by enzymatic hyaluronan synthesis. With hyaluronan brush heights in the micron range fabricated in less than an hour, the brushes of the invention have the distinct advantage that they can be directly visualized with fluorescence microscopy. This platform is an original technology for growing brushes, using neither the traditional grafting-to nor grafting-from methodology. To Applicant's knowledge the invention provides the thickest polymer brushes ever reported for synthetic or natural polymers (Zoppe J. O. et al., Surface-Initiated Controlled Radical Polymerization: State-of-the-Art, Opportunities, and Challenges in Surface and Interface Engineering with Polymer Brushes. Chemical Reviews 2017, 117(3): 1105-1318).

In certain embodiments, the present invention provides a polymer brush comprising: a substrate; and a plurality of hyaluronan synthase components attached to the substrate, at least some of the hyaluronan synthase components are capable of synthesizing a hyaluronic acid having a certain hydrodynamic diameter, wherein at least some of the hyaluronan synthase components comprise one or more hyaluronan synthase proteins in a fragment of cell membrane, the average distance between the hyaluronan synthase proteins in the fragment of cell membrane is substantially equal to or less than the average hydrodynamic diameter of the hyaluronic acid.

The invention also provides a polymer brush having a grafting density that is modified such that it comprises target regions comprising inactivated hyaluronan synthase components, wherein the inactivated hyaluronan synthase components are not capable of synthesizing polysaccharide.

The present invention further provides a polymer brush comprising: a substrate; and a plurality of hyaluronic acid polymers covalently attached to the substrate at certain grafting points on the substrate, wherein the average distance between the grafting points is substantially equal to or less than the average hydrodynamic diameter of the hyaluronic acid polymers.

In certain embodiments, the polymer brush serves as a lubricating agent, or a surface coating on an implant, a bandage or an anti-microbial surface.

In certain embodiments, the present invention also provides a method of preparing a polymer brush of comprising: providing a solution comprising a plurality of hyaluronan synthase components, at least some of the hyaluronan synthase components are capable of synthesizing a hyaluronic acid; and applying the solution to a substrate such that the plurality of hyaluronan synthase components are substantially immobilized on the substrate.

The substrate can be treated with a reaction mixture comprising uridine 5'-diphosphoglucuronic acid, or a salt thereof; uridine 5'-diphospho-N-acetylglucosamine, or a salt thereof; and $MgCl_2$, e.g., to provide a rapid polymerization. The polymerization can be substantially disrupted upon treatment with a quenching mixture (e.g., EDTA). The substantially disrupted polymerization can be reinitiated by replacing the quenching mixture with a reaction mixture (e.g., comprising uridine 5'-diphosphoglucuronic acid, or a salt thereof; uridine 5'-diphospho-N-acetylglucosamine; or a salt thereof; and $MgCl_2$).

In certain embodiments, the method of preparing the polymer brush further comprises a step of covalently binding the hyaluronic acid to the substrate to form a reinforced substrate comprising a plurality of covalently-bound hyaluronic acid polymers.

The present invention further provides a method of modifying the grafting density the polymer brush of the invention by: selecting a region of the polymer brush having a plurality of hyaluronan synthase components; and irradiating the region with UV light such that some of the plurality of hyaluronan synthase components in the target region become inactivated, wherein the inactivated hyaluronan synthase components are not capable of synthesizing polysaccharide.

The features and advantages of the present invention will be apparent to those skilled in the art. While numerous changes may be made by those skilled in the art, such changes are within the spirit of the invention.

DETAILED DESCRIPTION

Tailoring interfaces with polymer brushes is a commonly used strategy to create functional materials for numerous applications. Existing methods, however, are limited in brush thickness, the ability to generate high-density brushes of biopolymers, and the potential for regeneration. Here we introduce a scheme to synthesize ultra-thick regenerating hyaluronan polymer brushes using hyaluronan synthase. The platform provides a dynamic interface with tunable brush heights that extend up to 20 or even 50 microns (or larger)— several orders of magnitude thicker than standard brushes. The brushes are easily sculpted into micropatterned landscapes by photo-deactivation of the enzyme. Further, they provide a continuous source of megadalton hyaluronan or, can be covalently-stabilized to the surface. Stabilized brushes exhibit superb resistance to biofilms, yet are locally digested by fibroblasts.

The enzyme-generated giant polymer brush introduced here is distinct from traditional polymer brushes in several ways. Notably, rather than grafting from or grafting to the surface, the HA brush is generated by a transmembrane protein which extrudes the HA through a protein pore. The enzyme is able to polymerize much higher molecular weight molecules than other techniques such as free radical polymerization. Further, the polymer grows from the base of the interface rather than the tip of the polymer. The extraordinary brush height results in the unusual ability to directly visualize the brush with detailed spatial resolution. The enzymes also enable the option of brush regeneration.

This unique brush technology provides opportunities in a range of arenas including regenerating tailorable bio-interfaces for implants, wound healing or lubrication as well as fundamental studies of the glycocalyx and polymer physics.

A. Polymer Brush Compositions

Figure 1:
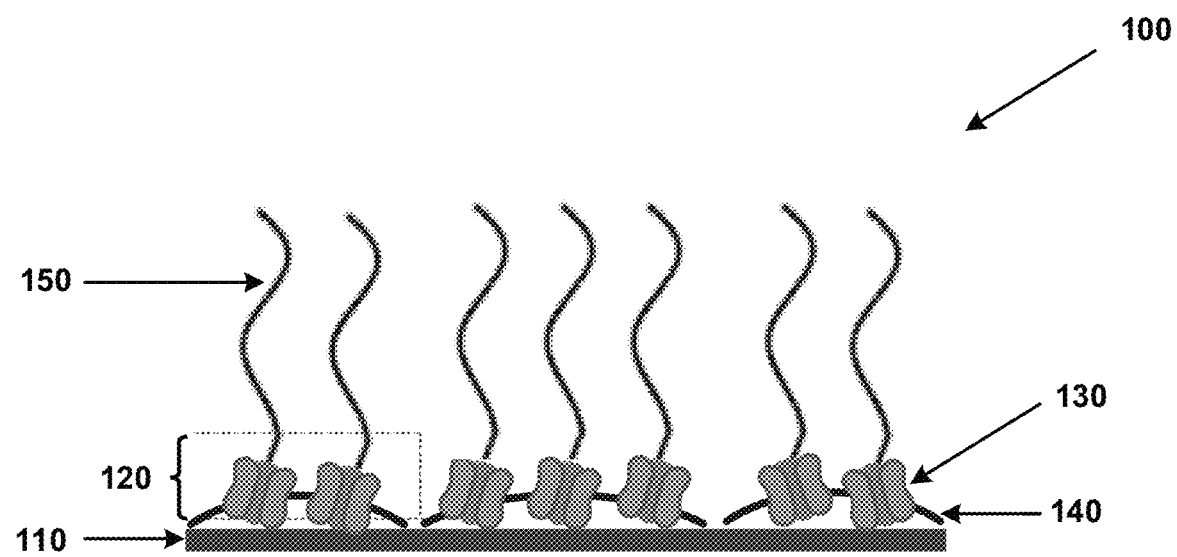
FIG. 1 is an example illustration of a polymer brush of the invention.

In some embodiments of the invention, the polymer brushes comprise a substrate (such as a glass or polymer surface) comprising a plurality of hyaluronan synthase components attached to the substrate, at least some of the hyaluronan synthase components are capable of synthesizing a hyaluronic acid. One exemplary embodiment of a polymer brush of the present invention is illustrated in FIG. 1. In this embodiment, a polymer brush 100 comprises a substrate 110 and a plurality of hyaluronan synthase components 120 (marked by dashed square) attached to the substrate 110. The hyaluronan synthase components 120 can comprise one or more hyaluronan synthase proteins 130 in a fragment of cell membrane 140. Additionally, at least some of the hyaluronan synthase components are capable of synthesizing a hyaluronic acid 150.

As used herein, the term "substrate" refers to a surface or layer that underlies something, or on which processes occur. In some embodiments, a substrate is a surface or material on which a protein can obtain nourishment and/or can carry out its enzymatic activity. The term "substrate" can also refer to, e.g., a surface or layer, e.g., a base surface or layer, on which another material is deposited. Exemplary substrates include, but are not limited to, glass, silicon, polymeric material, plastic, metallic materials (e.g., titanium-based materials), hydrogels, etc. Substrates can be slides, chips, particles, wells and the like.

The polymer brush constructs of the invention can further comprise a plurality of hyaluronan synthase components attached to the substrate. The term "hyaluronan synthase component" refers to a component having one more hyaluronan synthase proteins within a fragment of cell membrane (e.g., bacterial cell membrane). It has been discovered that hyaluronan synthase activity is robustly preserved in fragments of cellular membrane (e.g., bacterial membrane). For example, previous studies have used HA synthase-rich membrane fragments to investigate the function and kinetics of HA synthase, including the Group C *Streptococcus equisimilus* HA synthase (Baggenstoss B. A. et al., Size exclusion chromatography-multiangle laser light scattering analysis of hyaluronan size distributions made by membrane-bound hyaluronan synthase. Analytical Biochemistry 2006, 352(2): 243-251; Tlapak-Simmons V. L. et al., Kinetic Characterization of the Recombinant Hyaluronan Synthases from *Streptococcus pyogenes* and *Streptococcus equisimilis*. Journal of Biological Chemistry 1999, 274(7): 4246-4253). Typical bacterial membranes have a density of about 30,000 proteins/μm$^2$ (Quinn P. et al., Density of newly synthesized plasma membrane proteins in intracellular membranes II. Biochemical studies. The Journal of Cell Biology 1984, 98(6): 2142). In some embodiments, from about 2 to about 40% (or about 6% or about 7% or about 10%, or about 15%) of membrane proteins in the fragment of cell membrane by weight are HA synthase proteins. In some embodiments, about 2% to about 8% of membrane proteins in the fragment of cell membrane by weight are hyaluronan synthase proteins. In other embodiments, the average distance between the hyaluronan synthase components in the fragment of cell membrane is in the range of about 10 nm to about 50 nm, or about, 60 nm, or about 80 nm, or about 100 nm.

In some embodiments, the fragment of cell membrane can comprise a bacterial cell membrane. For example, the hyaluronan synthase proteins can be derived from *Streptococcus equisimilus* (Group C) hyaluronan synthase. In other embodiments, the fragment of cell membrane can comprise a mammalian cell membrane.

In some embodiments, the hyaluronan synthase components are attached to the substrate in such as way that they comprise about 10% to about 40%, or about 20% to about 80%, or even 100% of the surface area of the substrate. In some embodiments, the average distance between the plurality of hyaluronan synthase components on the substrates is less than about 1 µm, or less than about 0.5 µm or less than about 0.25 µm. In some embodiments, the hyaluronan synthase components are attached to the substrate such that the density of hyaluronan synthase proteins on the underlying surface is about 1000 molecules/m$^2$ to about 5000 molecules/µm$^2$ (or about 2100 molecules/µm$^2$). In some embodiments, the hyaluronan synthase component has an average diameter in the range of about 50 nm to about 500 nm, or about 100 nm, 120 nm, 140 nm, 145 nm, 150 nm, 160 nm, 180 nm, 200 nm, 250 nm, 300 nm, 400 nm or about 450 nm.

In some embodiments, the hyaluronan synthase components are substantially immobilized on the substrate. In some embodiments, the immobilization is an electrostatic absorption of the hyaluronan synthase components on the substrate.

Figure 7:
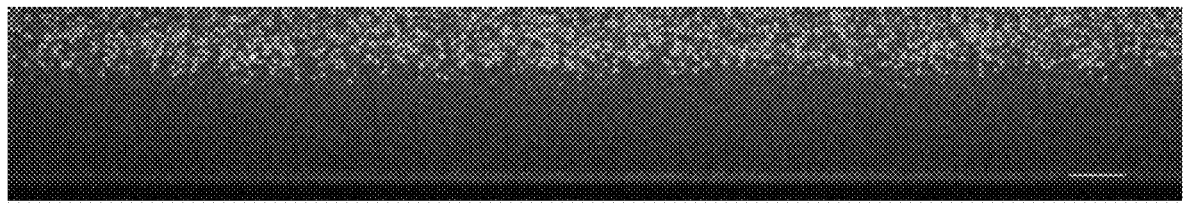
FIG. 7 shows a side view of a confocal image of an HA brush grown for 16 hours and imaged at low ionic strength (1.3 mM) (scale bar is 10 µm).

Surprisingly, even after the hyaluronan synthase components are attached to the substrates (and despite the underlying interface), Applicants have discovered that the UDP-sugar monomers are accessible to the enzyme which still manages rapid polymerization and extrusion of HA into the surrounding area. Indeed, the resultant hyaluronan synthase component are so extensive that the resulting brush can visibly excludes, e.g., 200 nm particles from the underlying substrate and establishes a giant gap of >20 microns in low ionic strength conditions (FIG. 7). Thus, at least some of the hyaluronan synthase components attached to the substrate are capable of synthesizing a hyaluronic acid having a certain hydrodynamic diameter, even after being bound to the substrate.

As used herein, the terms "hyaluronic acid," "hyaluronan," and "HA." which are used interchangeably herein, refer to a polymeric glycosaminoglycan, which contains repeating disaccharide units of N-acetyl glucosamine and glucuronic acid. Unless otherwise specified, the term "hyaluronic acid" encompasses all variants and combinations of variants of hyaluronic acid, hyaluronate or hyaluronan, of various chain lengths and charge states, as well as with various chemical modifications (such as an azide-modified hyaluronic acid). That is, the term also encompasses the various hyaluronate salts of hyaluronic acid with various counter ions, such as sodium hyaluronate.

The molecular weight of a single hyaluronic acid molecule of the invention is typically in the range of 0.1-10 MDa, but other molecular weights are possible. For example, in some embodiments, the average molecular weight of the hyaluronic acid is about 400 Da, or about 600 Da, or about 700 Da, or about 800 Da or about 900 Da or about 1 MDa, or about 2 MDa, or about 3 MDa, or about 4 MDa, or about 5 MDa, or about 6 MDa, or about 7 MDa, or about 8 MDa, or about 9 MDa, or about 10 MDa, or about 11 MDa, or about 12 MDa, or about 13 MDa, or about 14 MDa, or about 15 MDa. In other embodiments, the average size of the hyaluronic acid is less than about 12 MDa.

The average height of the hyaluronic acid synthesized by the plurality of hyaluronan synthase components is in the range of about 200 nm to about 50 µm, or about 250 nm, or at least about 300 nm, 400 nm, 500 nm, 600 nm, 700 nm, 800 nm, 900 nm, or at least about 1 µm. In some embodiments, the average height of the hyaluronic acid synthesized by the plurality of hyaluronan synthase components is in the range of about 500 nm to about 30 µm, or about 20 µm, or about 25 µm.

In some embodiments, the average height of the polymer brush itself is in the range of about 200 nm to about 50 µm, or about 250 nm, or at least about 300 nm, 400 nm, 500 nm, 600 nm, 700 nm, 800 nm, 900 nm, or at least about 1 µm. In some embodiments, the average height of the hyaluronic acid synthesized by the plurality of hyaluronan synthase components is in the range of about 500 nm to about 30 µm, or about 20 µm, or about 25 µm. In some embodiments, the hyaluronic acids are configured in the polymer brush structures in such a way that the average size of the polymer brush is in the range of about 500 nm to about 50 µm, or about 20 µm, or about 25 µm.

In some embodiments, the hyaluronic acid is defined in terms of its average hydrodynamic diameter. The hydrodynamic diameter refers to, e.g., the diameter of hyaluronic acid globules in solution. In some embodiments, the average hydrodynamic diameter of the hyaluronic acid is in the range of about 10 nm to about 50 µm, or about 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 160 nm, 170 nm, 180 nm, 190 nm, 200 nm, or about 250 nm, or about 300 nm, 400 nm, 500 nm, 600 nm, 700 nm, 800 nm, 900 nm, or about 1 µm. The hydrodynamic diameter of the hyaluronic acid can be measured using standard methods (such as light scattering) known to those skilled in the art. Polymer theory and experimental measurements show that the hydrodynamic radius scales with the molecular weight as $R_H \sim M^v$ where $0.7 < v < 0.8$ and M is the molecular weight (Cowman, Mary K., and Shiro Matsuoka. "Experimental approaches to hyaluronan structure." Carbohydrate research 340:5 (2005): 791-809).

In some embodiments, the average distance between the hyaluronan synthase proteins in the fragment of cell membrane is substantially equal to or less than the average hydrodynamic diameter of the hyaluronic acid. Without being bound by any theory of invention, Applicants have surprisingly discovered that polymer brushes having highly advantageous features, e.g., advantageous height and/or thickness values can be formed when the distance between hyaluronan synthase proteins in the fragment of cell membrane (and/or bound to the surface of the substrate) is substantially the same as or less than the hydrodynamic diameter of the hyaluronic acid formed by the plurality of hyaluronan synthase proteins on the substrate.

In some embodiments of the invention, the plurality of hyaluronic acid polymers are covalently attached to the substrate to form a polymer brush construct comprising: a substrate and a plurality of hyaluronic acid polymers covalently attached to the substrate at certain grafting points on the substrate. In certain embodiments, the average distance between the grafting points can be substantially equal to or less than the average hydrodynamic diameter of the hyaluronic acid polymers.

In some embodiments, the polymer brush is configured in such a way that it can be used as a lubricating agent, or a surface coating on an implant, a bandage or an anti-microbial surface.

B. Methods of Preparation

The present invention also provides methods for preparing polymer brush compositions of the invention. In certain embodiments, the polymer brushes can be prepared by, for example: providing a solution comprising a plurality of hyaluronan synthase components, at least some of the hyaluronan synthase components are capable of synthesizing a hyaluronic acid; and applying the solution to a substrate such that the plurality of hyaluronan synthase components are substantially immobilized on the substrate.

This invention makes use of the enzyme hyaluronan synthase which synthesizes hyaluronan through the cell's plasma membrane. In some embodiments, unique genetically modified bacteria are used to express hyaluronan synthase at high densities in their membranes. Small fragments of the bacteria membrane containing high density hyaluronan synthase (hyaluronan synthase components) can then be isolated and are bound to the substrate and/or interface of interest. In some embodiments, the high density hyaluronan synthase components can be prepared, e.g., from Sure II $E.$ $coli$ bacteria transfected with pKK223-3 vector or pBAD vector carrying HA synthase from $S.$ $equisimilis$, as described previously by Tlapak-Simmons V. L., et al. (J. Biol. Chem., 1999, 274, 4239-4245, the contents which are hereby expressly incorporated herein by reference). Suitable hyaluronan synthase genes and expression methods also include those described in U.S. Pat. Nos. 8,735,102; 7,504,246; 7,229,796; 7,166,450; 7,153,677; 7,141,409; 7,115,405; 7,109,011; 7,094,581; 7,091,008; 7,087,413; 7,060,466; 7,029,880; 7,026,159; 6,991,921; 6,951,743; 6,855,502; 6,852,514; 6,833,264; 6,455,304, each of which are hereby expressly incorporated herein by reference.

In some embodiments, the immobilization of the hyaluronan synthase components onto surfaces is achieved by electrostatically absorbing the components on the surface. For example, this can be done by first coating glass surfaces with a reagent such as polyethyleneimine (PEI) or the like and then activating with a reagent such as glutaraldehyde or the like. The primed surface can then be used to crosslink with the numerous proteins in the membrane fragments.

In some embodiments, the method further includes a step of treating the hyaluronan synthase-bound substrate with a reaction mixture comprising a nucleotide sugar substrate (e.g., uridine 5'-diphosphoglucuronic acid and/or uridine 5'-diphospho-N-acetylglucosamine or a salt thereof) to polymerize hyualuronic acid. In some embodiments, the nucleotide sugar substrate is selected from uridine 5'-diphosphoglucuronic acid trisodium salt or uridine 5'-diphospho-N-acetylglucosamine sodium salt. In some embodiments, the concentration of nucleotide sugar substrate in the reaction mixture is in the range of about 0.5 mM to about 100 mM, or about 1 mM to about 50 mM, or about 5 mM or about 8 mM, or about 10 mM. In some embodiments, the reaction mixture further comprises a source of magnesium, such as $Mg^{2+}$ or $MgCl_2$. In some embodiments, the reaction mixture is in the form of a saline solution. In some embodiments, the reaction mixture further comprises a salt such as sodium chloride, e.g., at a concentration of about 20 mM to about 150 mM.

In some embodiments, treating the substrate with a reaction mixture provides a rapid polymerization. For example, the polymerization can occur in less than 24 hours, or even less than 16 hours, or about 10 hours, or about 5 hours, or about 2 hours or about 1 hour or even less than about 1 hour.

In some embodiments, the polymerization of hyaluronic acid can be substantially disrupted, such that the degree of polymerization is reduced or even substantially terminated. The disruption can be permanent or a temporary disruption. Different means of disrupting the polymerization can be used, e.g., treating the substrate with a quenching mixture comprising EDTA at a sufficient concentration to lessen the enzymatic activity of hyaluronan synthase (e.g., about 10 mM to about 100 mM or about 30 mM to about 50 mM EDTA). The substantially disrupted polymerization can be reinitiated, in some embodiments, by removing EDTA or by replacing the quenching mixture with reaction mixture containing nucleotide sugar substrates and/or magnesium.

In some embodiments, hyaluronic acid polymerization and brush growth can be halted at a desirable height and, then later reinitiated by controlling the availability of $Mg^{2+}$ ions and sugar substrates.

In some embodiments, the hyaluronan synthase component maintains the ability to generate multiple polymers sequentially even after the natural release or external degradation of the hyaluronic acid (Baggenstoss B. A. et al., Size exclusion chromatography-multiangle laser light scattering analysis of hyaluronan size distributions made by membrane-bound hyaluronan synthase. Analytical Biochemistry 2006, 352(2): 243-251). Applicants have discovered that the polymer brushes of the invention can regenerate or continuously replenish hyaluronic acid as needed. For example, the brush can be grown for a certain period of time and then the generated hyaluronic acid can be removed by enzymatic degradation (hyaluronidase) and then regrown several times. Little deviation in final brush height from the initial height is detectable with each subsequent regeneration. Thus, the polymer brushes of the invention have the potential to be employed as regenerative interfaces.

Patterning polymer brushes is an important component of brush engineering for numerous applications (Nie Z. et al., Patterning surfaces with functional polymers. Nature Materials 2008, 7:277). The present invention provides a method to modify the grafting density and/or photopattern the polymer brushes by deactivating HA synthase function with UV irradiation or other similar means. As used herein, the term "grafting density" can refer to the concentration of activated hyaluronan synthase components per unit area on the substrate surface. The term "grafting density" can also be used to describe, for example, the concentration of polymers per unit area on a substrate surface. For example, a polymer brush of the invention can be prepared, in some embodiments, by: selecting a target region of the polymer brush having a plurality of hyaluronan synthase components; and irradiating the target region with a light source (e.g., UV light) such that the plurality of hyaluronan synthase components in the target region become inactivated, wherein the inactivated hyaluronan synthase components are not capable of synthesizing polysaccharide (or at least their production of polysaccharide is reduced). For example, Applicants have discovered that a confocal microscope equipped with, e.g., a 405 nm laser, and energy densities above 2.13E-04 Wsec/$um^2$ are sufficient to destroy HA synthase enzyme activity and prevent HA growth in micro-patterned regions. FIG. 22D shows a checkerboard pattern of the brush comprised regions with active HA synthase and other regions with no active HA synthase ($t_{growth}$=4 hrs, 130 mM). This simple, scalable method enables the complex (e.g., binary) patterning of HA polymer brushes, and can be extended to mask aligners to rapidly pattern larger areas. Such engineered interfaces are useful in various fields including controlling cell adhesion, tuning wettability, and indirectly modifying the height of brushes (Chen T. et al., Patterned polymer brushes. Chemical Society Reviews 2012, 41(8):3280-3296). The power density delivered to the HA synthase interfaces can be tuned to enable a simple approach to controlling its density, and consequently the brush grafting density.

Some applications like lubrication or anti-fouling interfaces or fundamental polymer physics studies, require a permanently stabilized brush. This is difficult to achieve with HA synthase binding alone, as the polymers release from the enzymes over a few days. Thus, the invention further provides a method to generate stabilized brushes by covalently crosslinking the HA to the surface. Covalent crosslinking can be achieved using standard coupling regents, such as, for example 1-Ethyl-3-(3-dimethylaminopropyl) carbodiimide (EDC), N-hydroxysuccinimide (NHS), and the like. For example, EDC can be used to activate the carboxyl groups on HA for conjugation to primary amine groups on the grafting surface.

The present invention also includes embodiments in which the hyaluronic acid is derivatized, for example, to produce a chemically reinforced polymer brush structure. An example of a derivatized brush includes azide-modified polymer brushes. It is well established that azido-substituted sugars such as N-azidoacetylgalactosamine (GalNAz) and N-azidoacetylmannosamine (ManNAz) can be incorporated into cell-surface oligosaccharides of varying types by natural glycosyltransferases (Laughlin, S. T. et al., Glycobiology, 2006, Vol. 415 Methods in Enzymology 230-250; Breidenbach, M. A. et al. Targeted metabolic labeling of yeast N-glycans with unnatural sugars, 2010, Proc. Natl. Acad. Sci. U.S.A. 107, 3988-3993). This technology has revolutionized the study of cellular glycobiology because the azide group can be selectively and rapidly captured by "click" reactions with strained-ring alkynes or terminal alkynes using copper-catalyzed azide-alkyne cycloaddition. (Prescher, J. A. et al., Chemical remodeling of cell surfaces in living animals. Nature, 2004, 430, 873-877; Koo, H. et al., Bioorthogonal copper-free click chemistry in vivo for tumor-targeted delivery of nanoparticles, Angew., Chem. Int. Ed., 2012, 51, 11836-11840).

Figure 35:
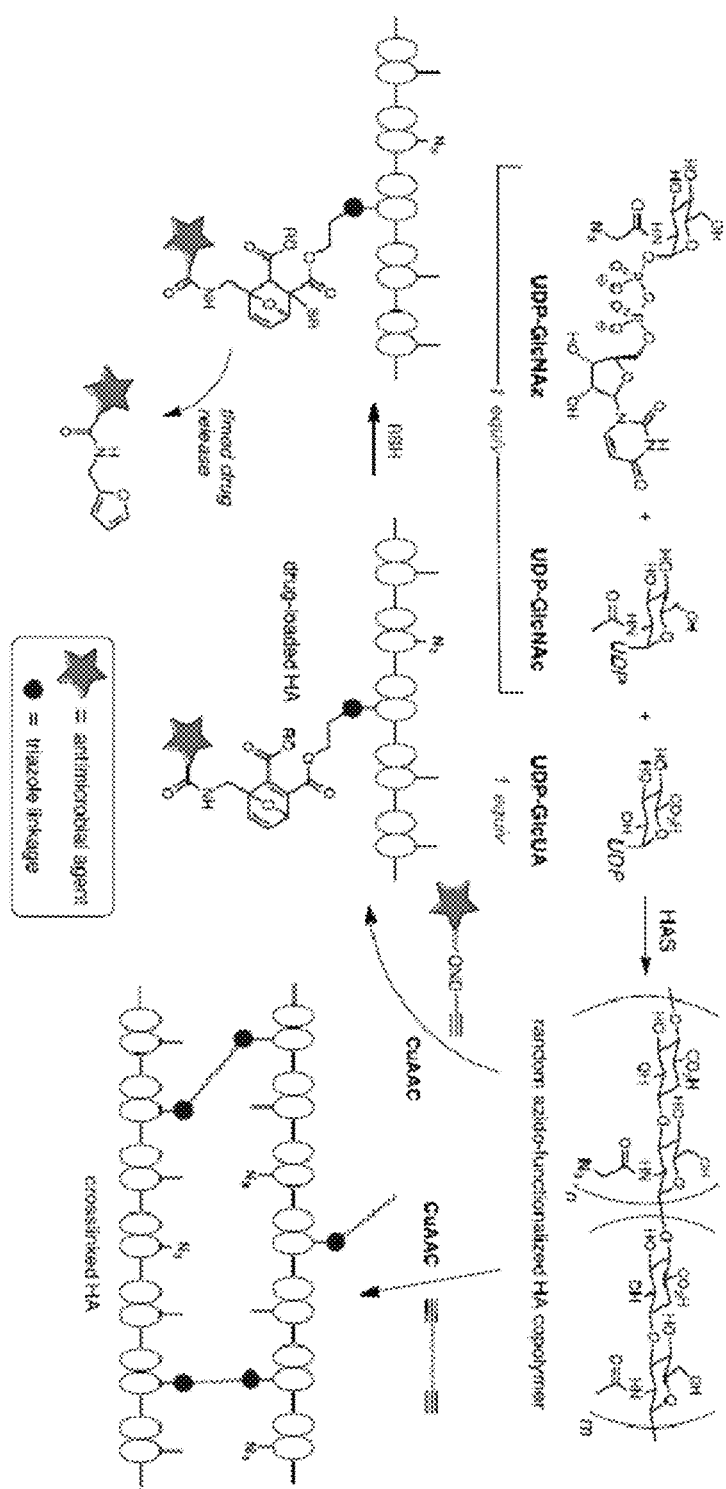
FIG. 35 is a schematic illustration of metabolic azide incorporation into hyaluronic acid and subsequent functionalization and crosslinking via copper-catalyzed azide-alkyne cycloaddition (CuAAC) and oxanorbornadiene (OND) chemistry.

FIG. 35 is a schematic illustration of metabolic azide incorporation into hyaluronic acid and subsequent functionalization and crosslinking via copper-catalyzed azide-alkyne cycloaddition (CuAAC) and oxanorbornadiene (OND) chemistry. As illustrated, azide-modified polymer brushes can be prepared using mixtures of natural and azide-modified a nucleotide sugar substrates (e.g., uridine 5'-diphosphoglucuronic acid, uridine 5'-diphospho-N-acetylglucosamine and uridine 5'-diphosph-N-azidoacetyl glucosamine) to polymerize hyaluronic acid. The azide-enriched brush can be further modified by copper-mediated reaction, e.g., with different types of alkynes (FIG. 35). Residual copper can be easily removed by washing with EDTA buffer. Terminal alkynes are easy to prepare, do not perturb the reaction site due to small size of the alkyne group, and rapidly attached. Strain promoted reaction can also be used.

Reaction with difunctional hydrophilic (e.g., PEG or oligopeptide) alkynes can be performed to crosslink the brushes and thereby protect them from digestion by hyaluronidase (HYAL) and/or to vary the mechanical properties. This is relevant for in vivo applications such as implants, drug delivery, medical devices, and tissue engineering. The crosslinked brushes can be characterized by measurement of thickness, concentration profile, permeability to molecules and nanoparticles, and resistance to HAdase digestion, as functions of crosslinking density.

Tunably cleavable oxanorboradiene technology can be used to attach and release functional molecules from these HA brushes (Kislukhin, A. A. et al., Degradable conjugates from oxanorbornadiene reagents. Journal of the American Chemical Society, 2012, 134, 6491-6497; Higginson, C. J. et al., Modular degradable hydrogels based on thiol-reactive oxanorbornadiene linkers. Journal of the American Chemical Society, 2015, 137, 4984-4987; Higginson, C. J. et al., Albumin-Oxanorbornadiene Conjugates Formed ex Vivo for the Extended Circulation of Hydrophilic Cargo. ACS Chemical Biology, 2016, 11, 2320-2327). These linkers can be programmed to undergo cleavage with half-lives from minutes to months, and slow release into the HA brush for applications such as antimicrobial interfaces, drug delivery, and implants are important applications of these thick, dense, and biocompatible brush polymer surfaces. Dyes and dye-labeled peptides can be used, as well as antimicrobial compounds. Dyes can also be attached via non-cleavable linkers to enable monitoring of HA stability in vivo.

C. Methods of Use

The polymer brushes of the present invention can be used in numerous ways, e.g., as functional materials such as lubricants, implant coatings, bandages and other uses.

In some embodiments, the polymer brush compositions of the invention are useful biomaterials such as implants and materials for the treatment of chronic wounds. The prevention of bacterial infection is another crucial aspect of both implants and wound treatments—in particular the problem of biofilm formation and adhesion. As described herein, the polymer brushes of the invention sterically exclude particles greater than 100 nm. Moreover, HA is a known anti-fouling polymer (Liu X. et al., Grafting hyaluronic acid onto gold surface to achieve low protein fouling in surface plasmon resonance biosensors. ACS applied materials & interfaces 2014, 6(15): 13034-13042; Ombelli M. et al., Competitive protein adsorption on polysaccharide and hyaluronate modified surfaces. Biofouling 2011, 27(5): 505-518; Park Y. D. et al., Photopolymerized hyaluronic acid-based hydrogels and interpenetrating networks. Biomaterials 2003, 24(6): 893-900; Glass J. R. et al., Characterization of a hyaluronic acid-Arg-Gly-Asp peptide cell attachment matrix. Biomaterials 1996, 17(11): 1101-1108). Applicants have examined whether the biofilm forming bacteria *Pseudomonas aeruginosa* (PAO1) are capable of irreversibly attaching to the brush and establishing a biofilm. As detailed below, both natural and reinforced brushes repelled the bacteria, natural brushes for at least 1 week (until the brush decays) and reinforced brushes for at least 2 weeks when the experiments ended. Few bacteria reached the underlying substrate in this time. In both cases, removing the bacteria from the surfaces was straightforward.

The HA film shows improved resistance to fouling, yet it still retains 6 times more bacteria than the HA brush (FIG. 24C) after both 1 and 5 day exposure. The antifouling properties of the brush can be complemented with doping the brush with anti-microbial compounds using straightforward and accessible chemistry associated with HA.

Further, the selective biointeractivity, i.e. inhibition of pathogenic microbial adhesion but enhancement of beneficial host cell responses, establishes the HA brush interface as an interesting option for coating for implants, bandages or other materials with similar requirements (Chua P-H et al., Surface functionalization of titanium with hyaluronic acid/chitosan polyelectrolyte multilayers and RGD for promoting osteoblast functions and inhibiting bacterial adhesion. Biomaterials 2008, 29(10): 1412-1421).

Binding the membrane fragments to other materials such as plastic or titanium, i.e. for catheters or implants, can be achieved using modified surface functionalization schemes.

Some challenges arise in the context of biomaterials applications of the polymer brushes of the invention and regeneration. One challenge is that bacterial membranes likely contain lipopolysaccharide (LPS) which could stimulate an immune response. One approach provided by the invention to bypass the LPS trigger includes the use of endotoxin-free bacteria which are nonimmunogenic (Mamat U. et al., Detoxifying *Escherichia coli* for endotoxin-free production of recombinant proteins. Microbial Cell Factories 2015, 14:57; Wilding K. M. et al., Endotoxin-free *E. coli*-based cell-free protein synthesis: Pre-expression endotoxin removal approaches for on-demand cancer therapeutic production. Biotechnology Journal 2018, 0(ja): 1800271). The invention also provides the use genetically engineered mammalian cells as the source of HA synthase, including HA generated from the future host of the biomaterial.

The HA brush platform also presents unique potential for fundamental polymer physics, where many open questions remain in the arena of polyelectrolyte brushes (Ballauff M. et al., Phase transitions in brushes of homopolymers. Polymer 2016, 98: 402-408; Xu X. et al., Structure and Functionality of Polyelectrolyte Brushes: A Surface Force Perspective. Chemistry—An Asian Journal 2018, 0(0)). The system enables the high-resolution visualization of brushes for the first time and ultimately, even dynamics of individual strands. For example, both polymer concentration profiles with height and particle penetration or protein absorption can be studied directly and compared with theory (de Vos W. M. et al., Interaction of Particles with a Polydisperse Brush: A Self-Consistent-Field Analysis. Macromolecules 2009, 42(15): 5881-5891). Schemes to fluorescently label only the tip of the brush as it extrudes, by for example stopping after small growth, and then continuing growth after labeling, are provided by the invention which facilitate dynamic studies of individual polymer strands and/or the ends of the polymers that were previously inaccessible (Murat M. et al., Structure of a grafted polymer brush: a molecular dynamics simulation. Macromolecules 1989, 22(10): 4054-4059).

Engineered biomaterials based on HA are abundant in the literature and medical practice. The regenerative HA brush interface introduced here represents a new platform for creating a distinct class of interfacial HA biomaterials. The straightforward and established protocols to chemically modify and crosslink HA presents numerous opportunities for exploration and expansion of traditional approaches (Highley C. B. et al., Recent advances in hyaluronic acid hydrogels for biomedical applications. Current Opinion in Biotechnology 2016, 40: 35-40; Zheng Shu X. et al., In situ crosslinkable hyaluronan hydrogels for tissue engineering. Biomaterials 2004, 25(7): 1339-1348). The regenerative ability of the platform is a unique aspect of the invention, as are the novelty and distinct properties of a gigantically thick brush. From lubrication to antifouling to molecular filtration, the unusual characteristics of this brush motivate a plethora of useful applications. In addition to these applications, the brush also enables fundamental studies of polyelectrolyte brushes as well as the cell glycocalyx, which plays an important but poorly understood biophysical role in the body (Kuo J C-H. et al., Physical biology of the cancer cell glycocalyx. Nature Physics 2018, 14(7): 658-669).

The invention will be described in greater detail by way of specific examples. The following examples are offered for illustrative purposes and are not intended to limit the invention in any manner. Those of skill in the art will readily recognize a variety of noncritical parameters which can be changed or modified to yield essentially the same results.

EXAMPLES

Reagents used below can be obtained from commercial sources such as Sigma-Aldridge and EMD Biosciences. Imaging experiments were conducted using the parameters described in the examples below.

Example 1

HA Synthase Enriched Bacterial Membrane Fragments

This example describes the preparation of HA synthase enriched bacterial membrane fragments. HA synthase open reading frames from *Streptococcus equisimilus* were inserted into the pKK223-3 vector of *E. coli* SURE™ cells as described previously (Tlapak-Simmons V L, et al., 1999, Purification and lipid dependence of the recombinant hyaluronan synthases from *Streptococcus pyogenes* and *Streptococcus equisimilis*, Journal of Biological Chemistry 274(7), 4239-4245). The bacteria were grown to $OD_{600}$ 1.6 at which point HA synthase production was induced for three hours. The bacteria were then centrifuged at 4° C. for 5 min at 5000 rcf. The bacteria pellet was resuspended in the lysis buffer, comprised of 50 mM HEPES (Research Products International Corp H75030), 500 mM NaCl (OmniPure 7710), 10% glycerol (Invitrogen 15514-011), 1 mM phenylmethane sulfonyl fluoride (PMSF) (Sigma-Aldrich P7626, diluted with anhydrous isopropyl alcohol), DNAase (Roche 10104159001), and lysozyme (Roche 10837059001) at pH 7.4; and then stirred for 30 mins at 4° C. The bacteria were then sonicated in 3.5 mL aliquots three times for 30 seconds each with 1 min rest time between sonications. The sonicated bacteria were centrifuged at 4° C. for 30 mins at 5000 rcf. The supernatant was retained, and the pellet discarded. The supernatant was then ultracentrifuged at 4° C. for 1 hr at 35,000 rpm. The supernatant was discarded and the resulting pellet was stored in lysis buffer and 1 mM PMSF in a −80° C. freezer. The concentration of the resulting fragments was determined via Bradford Assay.

Next, the membrane fragments were characterized by scanning electron microscopy and dynamic laser scattering. The membrane fragment suspension was removed from the −80° C. freezer and defrosted. Then, it was diluted from 1 mg/mL to a final concentration of 0.02 mg/mL with phosphate buffer (pH 7.3, 75 mM $NaKPO_4$, $Na_2HPO_4$ (J. T. Baker 3827-01), $KH_2PO_4$ (Sigma-Aldrich P5655) together with 0.1 mM EDTA (Mallinckrodt Chemicals 2590-12), 50 mM NaCl, 2% glycerol, 5 mM DTT (Sigma-Aldrich D9779). The membrane fragments were then attached on a spherical or planar surface as described in Example 2.

Figure 2:
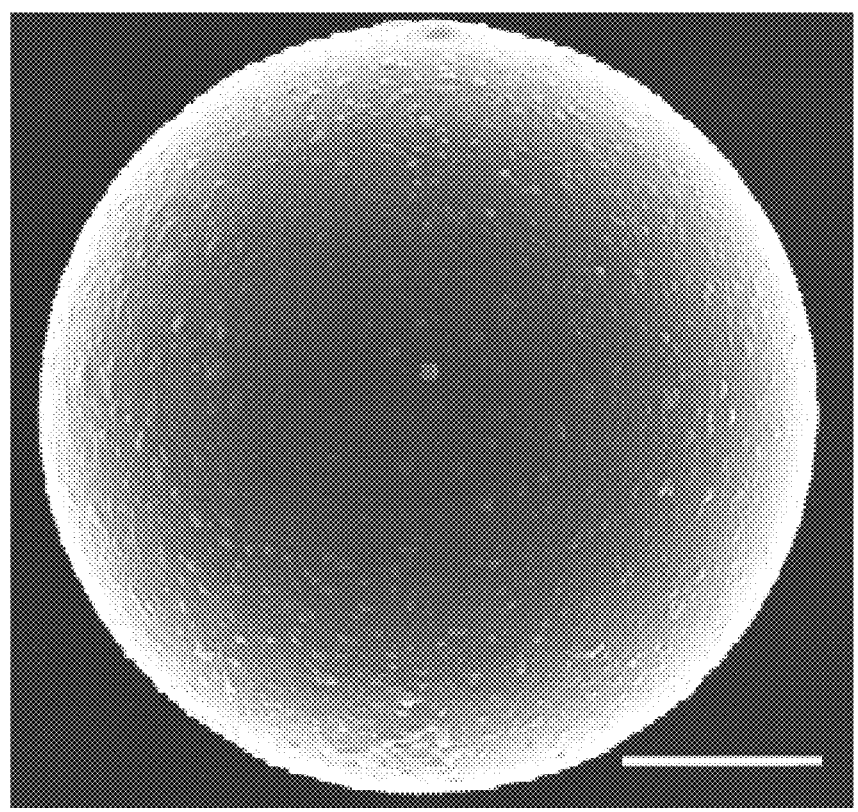
FIG. 2 is a scanning electron microscopy image of membrane fragments on a spherical surface (scale bar is 2 µm).

Dynamic light scattering was performed and analyzed using a Malvern ZetaSizer Nano ZS. The autocorrelation function was acquired every 10 seconds with 10 measurements for each of three runs. The intensity of light was collected at a scattering angle of 90°. Analysis yielded an average membrane fragment diameter of ~145 nm (before HA growth) (FIG. 2, scale bar is 2 μm).

Figure 3:
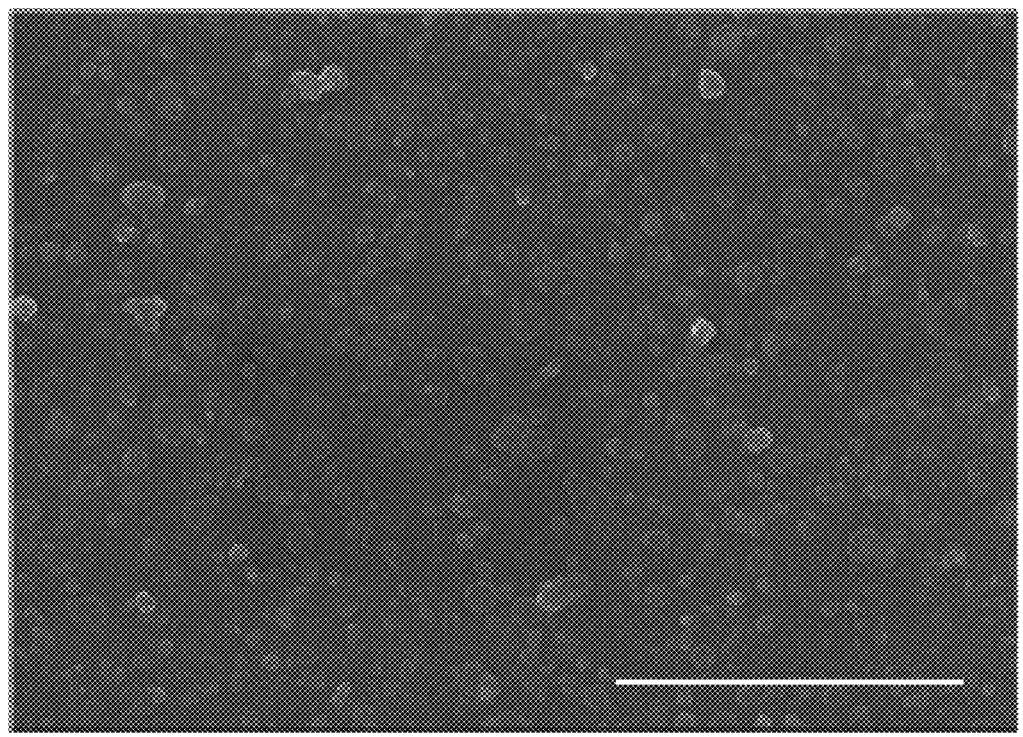
FIG. 3 is a scanning electron microscopy image of membrane fragments on a planar glass surface (coverslip) (scale bar is 2 µm). Red in image is artificial outlines of the membrane fragments.

A scanning electron microscopy (SEM) image of the membrane fragments on a planar glass surface (coverslip) is shown in FIG. 3 (scale bar is 2 μm). Segmentation analysis estimates that ~30% of the surface area is decorated with HA synthase fragments. The average size of the fragments is ~100 μm which is consistent with measurements using dynamic light scattering.

Figure 4:
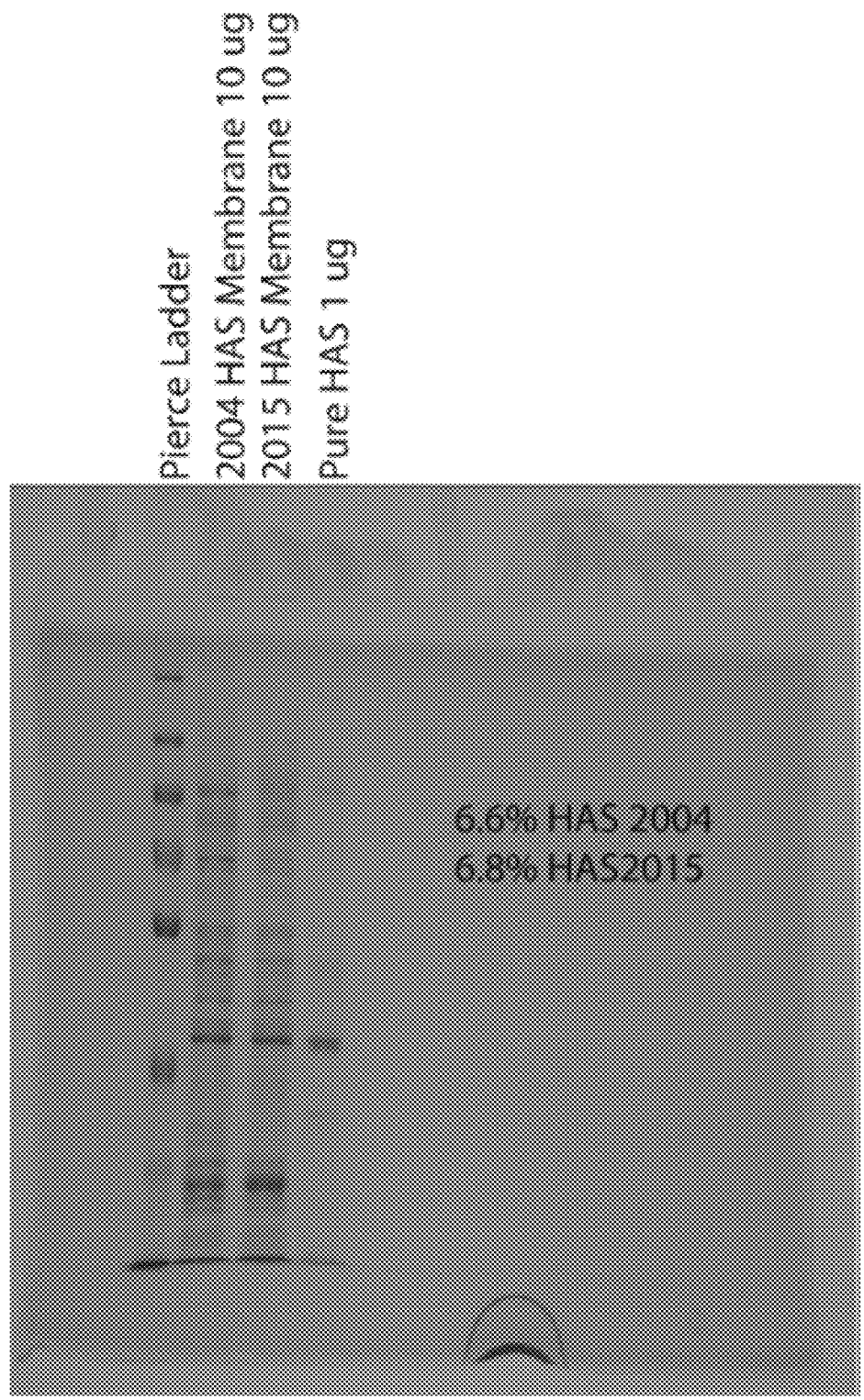
FIG. 4 shows the results of an experiment in which protein content in HA synthase fragments is measured by gel electrophoresis.

Gel electrophoresis was performed to determine the total protein content of the HA synthase membrane fragments. Along with membrane fragments that were prepared in 2004 and 2015, purified HA synthase was also run for comparison. By comparing pixel density in each column, it is estimated that 6.8% of the protein present in the 2015 HA synthase membrane fragments are the HAS itself. The 2015 membrane fragment supply was used for all experiments presented here. Protein content in HA synthase fragments as measured by gel electrophoresis is shown in FIG. 4.

Example 2

Procedure for Binding HAS Fragments to Glass

Figure 5:
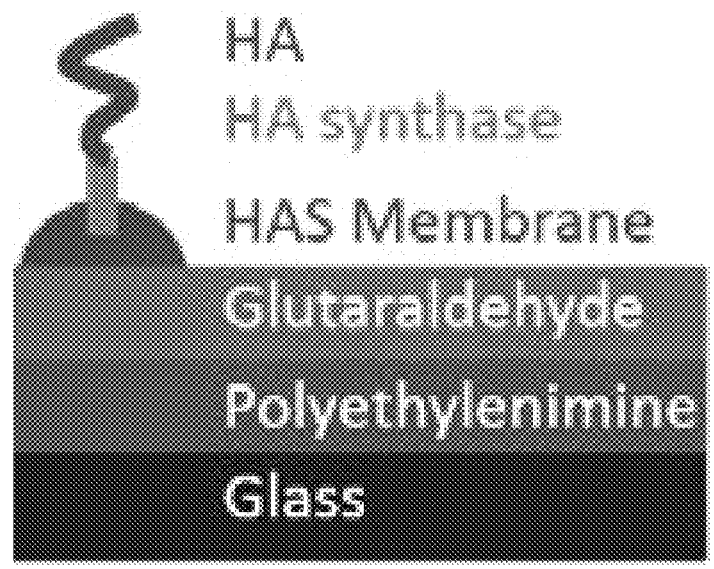
FIG. 5 is an illustration showing a glass surface coated with polyethyleneimine (PEI) and glutaraldehyde which forms a covalent crosslinking with amine functional groups of HA synthase membrane fragments

This example describes the binding of the HAS-active membrane fragments to a glass interface. In general, the glass surface was coated with polyethyleneimine (PEI) and then activated with glutaraldehyde which formed a covalent crosslinking with amine functional groups of the membrane fragments (FIG. 5).
A. Immobilization on Glass Slides:
Coverslips (VWR 48366 246 or VWR 48366 067) were sonicated in ultrapure water for 15 min and cleaned in reagent grade acetone in a sonicating water bath for 15 minutes. The coverslips were then rinsed with ultrapure water and dried with nitrogen and treated in a plasma cleaner (Harrick Plasma, PDC-32G, High RF power, air, 1 min). Poly(ethyleneimine) (PEI) (Sigma 482595, average Mw 1.3 kDa, 50% w/v in water) was diluted with ultrapure water to 2.5% and the pH was adjusted to 7.0 using HCl. 200 μL PEI was used to cover each coverslip (facing up) after plasma cleaning. The coverslips were incubated for one hour before they were rinsed with ultrapure water and dried with nitrogen. Glutaraldehyde (Sigma G7651, average MW 0.1 kDa, 50% w/v in $H_2O$) was diluted to 2.5% with PBS. 200 μL glutaraldehyde was sandwiched between a piece of parafilm and the coverslip, with the PEI coated side facing the solution. The coverslips were incubated for one hour before they were rinsed with ultrapure water and dried with nitrogen. The coverslips were then mounted on custom Teflon rings using vacuum grease to seal. 30 μL of 0.2 mg/mL HA synthase-rich bacterial membrane fragments (diluted from 1 mg/mL in phosphate buffer) was pipetted into each teflon ring. The coverslips were incubated for one hour. The solution in the sample holder was exchanged four times with Tris storage buffer (pH 7.3, 50 mM Tris (BDH 0312), 500 mM NaCl, 20 mM DTT, 5% glycerol). The samples were stored at −20° C.
B. Immobilization on Silica Microspheres:
In a 90° C. water bath on a stirring hot plate, 100 mg monodisperse silica beads (Cospheric LLC, 1.8 g/cm$^3$, 7.75 μm diameter, CV=3.7%, <1% doublets) were added to 1 mL 30% 14202 in a 1.5 mL centrifuge tube. The beads were briefly vortexed to suspend them and then the tube was put in a sonicating water bath for 15 minutes to disperse the beads. A stir bar was added along with 3 mL sulfuric acid (BDH Aristar Plus, average Mw 0.98 kDa) in a disposable glass vial (22 mL, VWR 470206-384). The 1 mL beads suspended in 30% $H_2O_2$ were gently pipetted into the vial while allowing slow stirring. The vial was secured with a clamp in the stirring hot water bath. The piranha cleaning was allowed to proceed for 2 hours during which the level of the water bath is maintained. Finally, 10 mL ultrapure water was slowly added to the vial, allowing the water to fully mix. Heating and stirring was turned off and the vial was allowed to sit overnight to let the microspheres to settle. On the next day, most of the piranha solution was removed using a glass pipette tube. The beads were resuspended with stirring and then transferred to a glass centrifuge tube. Using a swing bucket centrifuge, the solution was exchanged with ultrapure water seven times and checked to ensure that the pH of the solution was above six. After supernatant removal, the beads were suspended in 2.5% w/v PEI and then stirred for 1 hour before washing 7 times with ultrapure water. Glutaraldehyde was added to a final concentration of 2.5% w/v with PBS to a clean glass vial. The washed beads were slowly added and the suspension was allowed to stir for 1 hour before washing 7 times with ultrapure water. To prepare the membrane fragments for deposition on glutaraldehyde-modified beads, the Tris-based membrane fragment storage buffer was exchanged with a phosphate buffer using a Slide-A-Lyzer™ MINI Dialysis Device (Thermo Scientific 69570) in an ice box (4° C.). The phosphate buffer was refreshed twice in 45 min intervals. The fragments were transferred to a 1.5 mL centrifuge tube and the activated silica beads were slowly added. The centrifuge tubes were placed in a tube rotator and set to slow rotation for 2 hours at 4° C. The beads were allowed to settle and then the supernatant was removed. The beads were exchanged into the Tris storage buffer by adding the buffer, allowing the beads to settle, and removing the supernatant three times. Finally, the beads were aliquoted in storage buffer and stored in −80.0 freezer.

The HAS activity from glass-bound fragments was verified as described in Example 3.

Example 3

Activating HA Synthesis in Membrane Fragments

Activation of HA synthase in membrane fragments was achieved by exchanging the storage buffer of the membrane fragment suspension prepared in Example 1 with activation buffer (pH 7.3, 75 mM NaKPO$_4$, 50 mM NaCl, 20 mM MgCl$_2$, 0.1 mM EDTA). After warming the sample for 45 min in a 30° C. incubator, uridine 5-diphosphoglucuronic acid trisodium salt (UDP-GlcUA, Sigma-Aldrich U6751) and uridine 5-diphospho-N-acetylglucosamine sodium salt (UDP-GlcNAc, Sigma-Aldrich U4375) were added at 0.5 mM to 1.5 mM each. HA synthesis was quenched by exchanging the activation buffer with quenching buffer (pH 7.3, 75 mM NaKPO$_4$, 50 mM NaCl, 20 mM EDTA) via mixing by gently pipetting the liquid up and down. The buffer exchange was repeated seven times.

Example 4

HA Purification for Solid-State Nanopore Analysis

In this Example, HA grown from bacterial membrane fragments in suspension was purified for later quantification by solid state nanopore. Specifically, after HA production, EDTA was added to a final concentration of 40 mM to quench the growth and the solution was put on ice for 10 mins. The solution was then placed on a 90° C. heat block for 10 mins and subsequently put on again for 1-2 mins to inactive the HA synthase (Weigel P. H., et al., Hyaluronan synthase polymerizing activity and control of product size are discrete enzyme functions that can be uncoupled by mutagenesis of conserved cysteines, *Glycobiology* 2012, 22(10): 1302-1310). To dissociate HA from the synthase, the solution was mixed in a 3:1 ratio of Folch to HA solution and allowed to shake for 15 mins. The Folch/HA solution was centrifuged for 7 mins at 8,000 rpm and then the supernatant containing HA was removed and speed vacuumed until the solution volume was reduced to one-third.

Example 5

Solid-State Nanopore Determination of HA Molecular Weight Distribution

Figure 6:
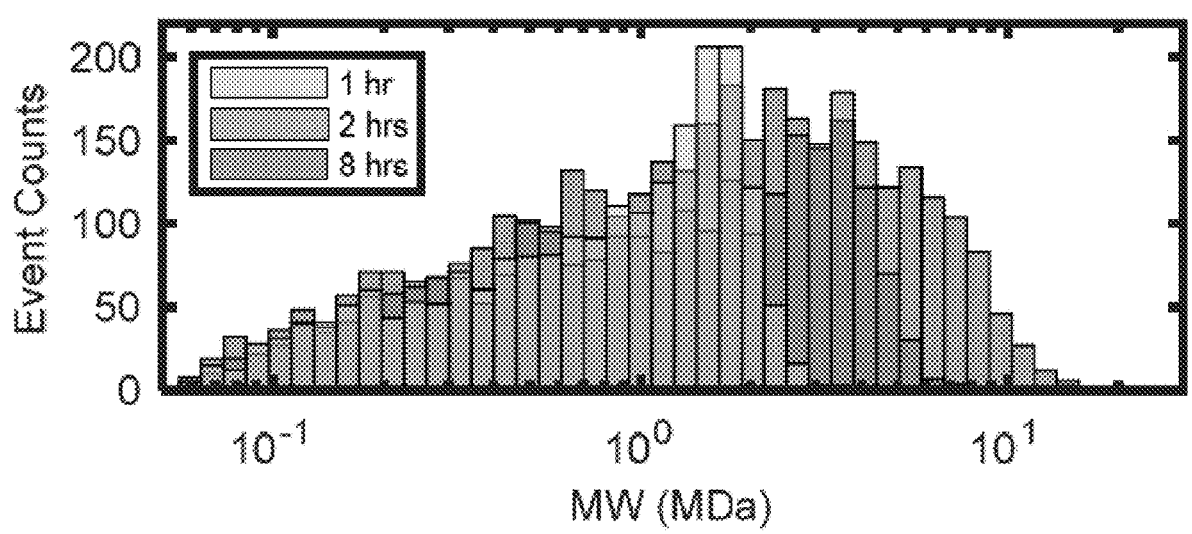
FIG. 6 shows HA molecular weight distributions fabricated by HA synthase assayed by solid state nanopore (N=2093, 1 hr; N=2503, 2 hrs; N=3701, 8 hrs).

Enzymatically-generated HA samples were mixed with measurement buffer (6M LiCl, 10 mM Tris, 1 mM EDTA, pH 8.0) to a final concentration of 30 ng/μl and stored at −20° C. until measurement. Solid-state nanopore analysis was performed on 10 μl aliquots of the samples as described previously (Rivas F. et al., Label-free analysis of physiological hyaluronan size distribution with a solid-state nanopore sensor. Nature Communications, 2018, 9(1):1037). Briefly, a single pore (6-8 nm diameter) was fabricated (Jijin Y. et al., Rapid and precise scanning helium ion microscope milling of solid-state nanopores for biomolecule detection. Nanotechnology 2011, 22(28):285310) in a 19 nm thin, free standing silicon nitride membrane supported by a silicon chip (4 mm) and was placed in between one reservoir of clean measurement buffer and one reservoir of sample mixture. Ag/AgCl electrodes (Sigma Aldrich, St. Louis Mo.) were placed in each reservoir and an Axopatch 200b patch clamp amplifier (Axon Instruments, Union City, Calif.) was used to both apply a voltage of 200 mV and record transpore ionic current and resistive pulses caused by HA translocation through the pore. Data was collected at a rate of 200 kHz with a four-pole Bessel filter and an additional 5 kHz low-pass filter was applied using custom software. Resistive pulses ('events') in the current signal were identified as transient interruptions in the ionic current >5σ in amplitude from the baseline and with a time duration range of 25 μs-2.5s. The Event Charge Deficit (ECD66) (defined as the integrated area of the event) was determined for each translocation event and converted to molecular weight using a calibration standard produced with synthetic, quasi-monodisperse HA (Rivas F. et al. Label-free analysis of physiological hyaluronan size distribution with a solid-state nanopore sensor. Nature Communications 2018, 9(1):1037). A MW distribution histogram was generated for each sample with these values and used for subsequent analyses. FIG. 6 shows HA molecular weight distributions fabricated by HA synthase assayed by solid state nanopore (N=2093, 1 hr; N=2503, 2 hrs; N=3701, 8 hrs).

Example 6

Scanning Electron Microscopy

Membrane fragments were immobilized on 5 mm by 5 mm by 1 mm glass slides (VWR 16004-430) using the methods described above. Next, the slides were immersed in 2.5% w/v glutaraldehyde in PBS for 1 hr. Then, the slides were rinsed with ultrapure water and air-dried. Finally, the slides were coated with carbon using chemical vapor deposition (Cressington 108A carbon coater) and imaged with a Scanning Electron Microscopy (Zeiss Ultra 60 SEM).

Example 7

Confocal Imaging

Fluorescent characterization of the HA brush was made using a scanning laser confocal microscope (FV1000, Olympus, Tokyo, Japan; Objective: PlanApo N, 60×/1.42 NA oil). When imaging planar polymer brushes, a 100 nm vertical step was used and a 20 μm thick z-stack was taken of the planar brush. When imaging the polymer brushes on microspheres, a 30 nm to 60 nm horizontal pixel size and 470 nm vertical step was used. A four micron thick z-stack was taken for each microsphere. The vertical range was selected to, at minimum, to measure to slightly above the bead center. Imaging was completed within 1 h after quenching HA synthesis in order to avoid significant desorption of the HA polymers. FIG. 7 shows a side view of a confocal image of an HA brush grown for 16 hours and imaged at low ionic strength (1.3 mM) (scale bar is 10 μm). The brush region is inferred by contrast generated by its accessibility to fluorescent dextran (cyan, 10 kDa) but exclusion of nanoparticles (red, 200 nm). The brush height shown is about 22 μm.

Example 8

HA Brush Concentration Profile Analysis

The concentration profile of the HA brush is estimated by looking at the fluorescent intensity generated by GFPn, a protein that binds to HA. The GFPn is comprised of green fluorescent protein (GFP) with the HA-linking domain of neurocan connection, specifically binds to HA (Zhang H. et al., Neurocan-GFP Fusion Protein: A New Approach to Detect Hyaluronan on Tissue Sections and Living Cells. Journal of Histochemistry & Cytochemistry 2004, 52(7): 915-922). GFPn was expressed by HEK 293 EBNA cells purified according published protocols (McLane L. T. et al., Spatial Organization and Mechanical Properties of the Pericellular Matrix on Chondrocytes. Biophysical Journal 2013, 104(5): 986-996; Boehm H. et al., Mapping the mechanics and macromolecular organization of hyaluronan-rich cell coats. Soft Matter 2009, 5(21): 4331-4337). In experiments where HA-GFPn profiles were assayed, we incubated with 8 mg/mL BSA for 40 min to backfill the surface before HA synthesis. This reduces the adhesion of GFPn to the underlying substrate. Before starting the HA synthesis, the BSA solution was removed. After quenching HA synthesis, we added ~44 μM GFPn to final concentration of 3 μM GFPn. For planar brushes, the z fluorescence profile was extracted from confocal microscopy z-stacks.

For spherical brushes, the centers of the microspheres are identified by segmenting either the image of the dextran channel or the GFPn channel using Otsu's method (Otsu N. A threshold selection method from gray-level histograms. IEEE transactions on systems, man, and cybernetics 1979, 9(1): 62-66). An azimuthally averaged profile was extracted from 30 degree cones from the center of a microsphere, only analyzing the cones which are clear of neighboring brushes. The mean background (and its standard deviation) was determined from the last 50 data points at the edge of the image (away from the microsphere). The edge of the brush was defined where the intensity is greater than or equal to twice the standard deviation above the mean background. The peak in the GFPn was identified as the surface of the microsphere. The thickness of the brush measured using 200 nm particle exclusion assays is 3.75±0.30 μm ($N_{beads}$=146) is consistent with the value measured using GFPn of 3.70±0.25 μm ($N_{beads}$=112) for non-reinforced brushes on eight-micron diameter particles ($t_{growth}$=4 hrs, high salt condition).

Figure 8:
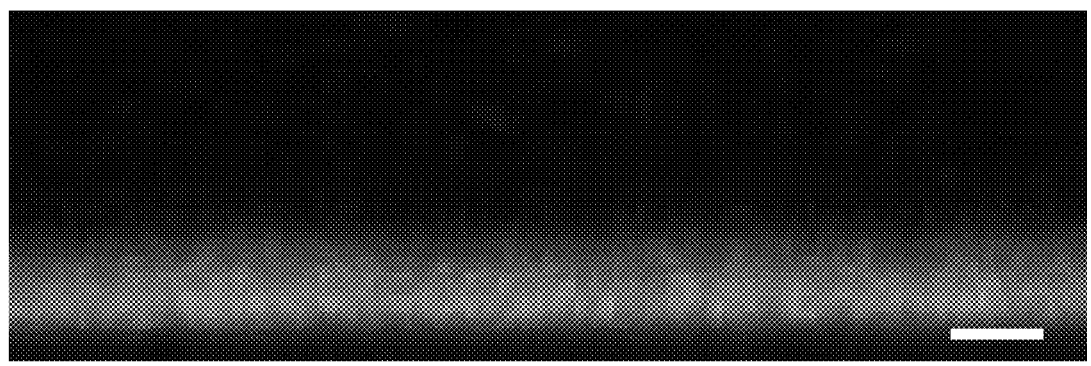
FIG. 8 illustrates a fluorescent profile of a planar HA brush (A) and its intensity profile (B) (scale bar is 5 µm).
Figure 8:
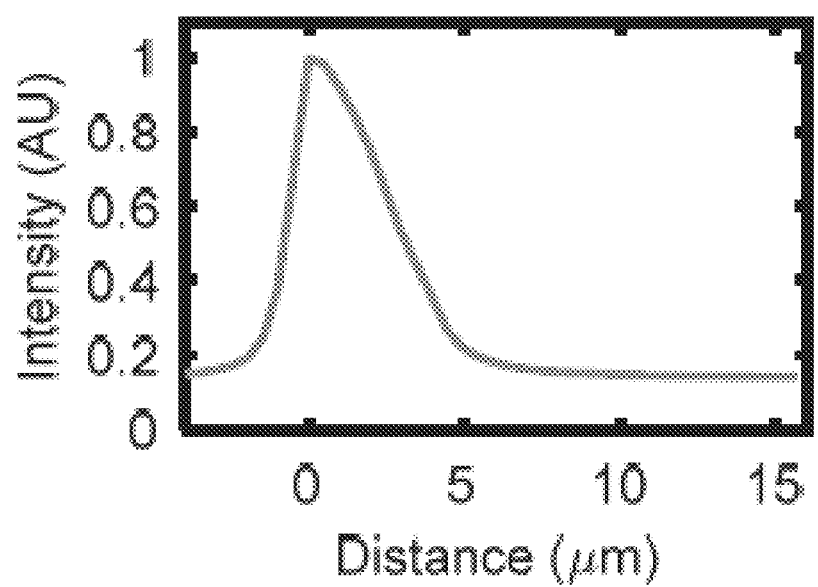
Figure 9:
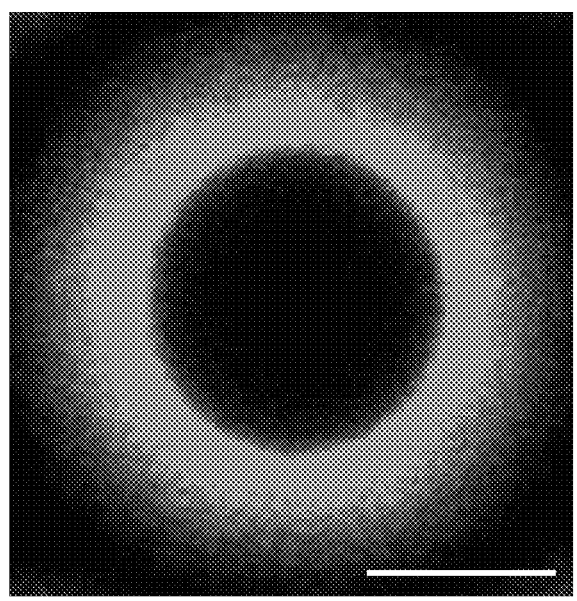
FIG. 9 illustrates a fluorescent profile of a spherical brush (A) and its intensity profile (B) (scale bar is 5 µm).
Figure 9:
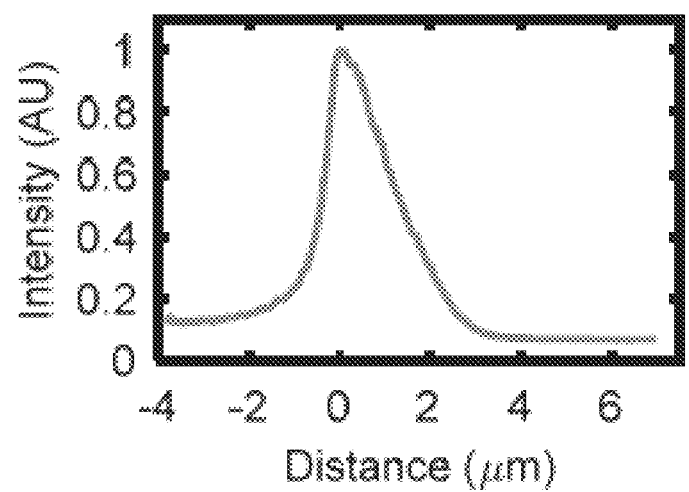
Figure 10:
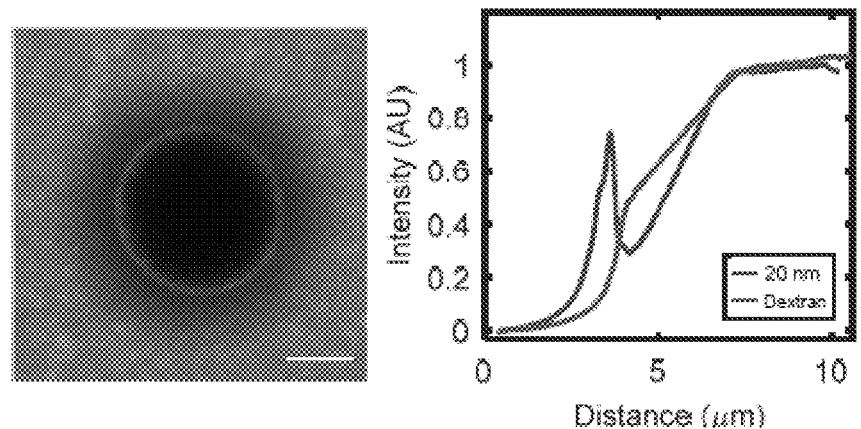
FIG. 10 illustrates a cross-section of brush grown for 4 hours on an 8 µm microsphere (left) and the particle penetration intensity profile (right) for 20 nm particles, 130 mM ionic strength (A), 200 nm particles, 130 mM ionic strength (B), and 200 nm particles, 1.3 mM ionic strength (C) (scale bar is 5 µm).
Figure 10:
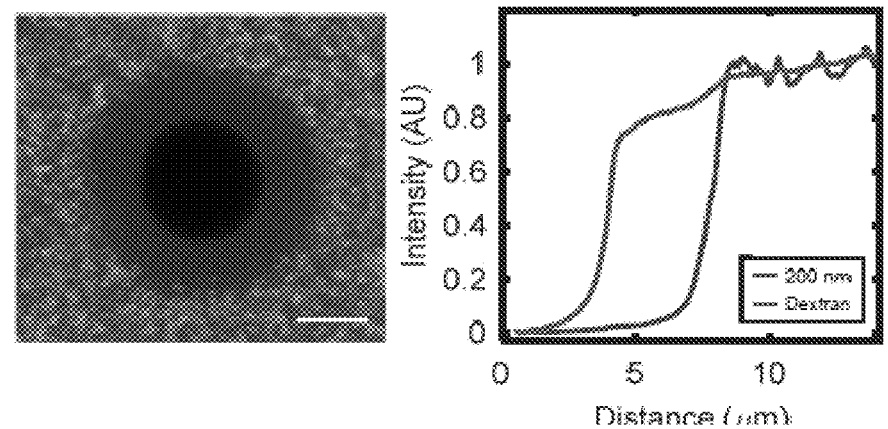
Figure 10:
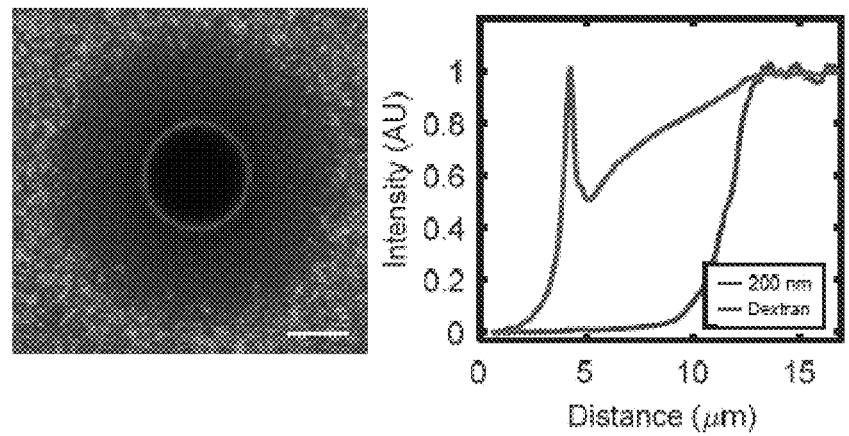
Figure 11:
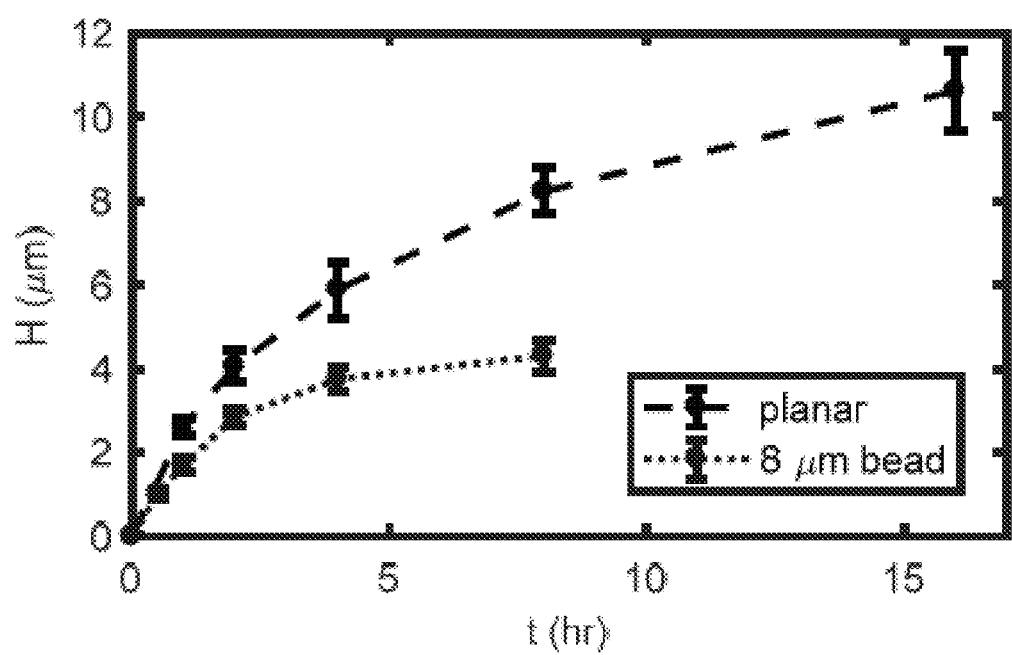
FIG. 11 illustrates the dynamic growth of HA brushes generated by HA synthase (133 mM).

FIG. 8 illustrates a fluorescent profile of a planar HA brush (A) and its intensity profile (B) (scale bar is 5 μm). FIG. 9 illustrates a fluorescent profile of a spherical brush (A) and its intensity profile (B) (scale bar is 5 µm). In both FIG. 8 and FIG. 9 the brush growth time is 4 hours at 30° C. and the ionic strength is 130 mM. FIG. 10 illustrates a cross-section of brush grown for 4 hours on an 8 µm microsphere (left) and the particle penetration intensity profile (right) for 20 nm particles, 130 mM ionic strength (A), 200 nm particles, 130 mM ionic strength (B), and 200 nm particles, 1.3 mM ionic strength (C) (scale bar is 5 µm). The 20 nm particles show a distinct gradient within the brush while 200 nm particles remain excluded. Dextran (10 kDa, ~5 nm) is present in all cases (cyan) and shows an enhanced gradient (C) in the low ionic strength swollen brush. FIG. 11 shows the dynamic growth of HA brushes generated by HA synthase (133 mM). The brush height reaches 2.62±0.22 µm in just 1 hour (planar) in high ionic strength conditions. After 16 hours the brush is 10.6+/−1.0 µm. N=3 brushes, 12 regions per sample. The spherical brush plateaus at much earlier times (~5 hrs) at a final height of 4.3+/−0.4 µm. N>120 for spherical brush height measurements.

Example 9

Particle Exclusion and Nanoparticle Penetration Assays

Particle exclusion assays were performed by adding red 200 nm FluoSpheres (carboxylate-modified Molecular Probes, Inc., catalog number: F8810) to a final concentration of 0.7% w/v along with fluorescent dextran (Molecular Probes, Inc. Alexa Fluor 647, 10 kDa) to a final concentration of 33 µg/mL. Nanoparticle penetration was investigated using the red, 200 nm FluoSpheres, green 100 nm Fluospheres (Catalog number: F8803), and green 20 nm Fluospheres (Catalog number: F8787). When the grafting surface needed to be labeled, 0.007% w/v of the green, 20 nm nanoparticles were added.

Example 10

Hyaluronan Brush Characterization

Figure 12:
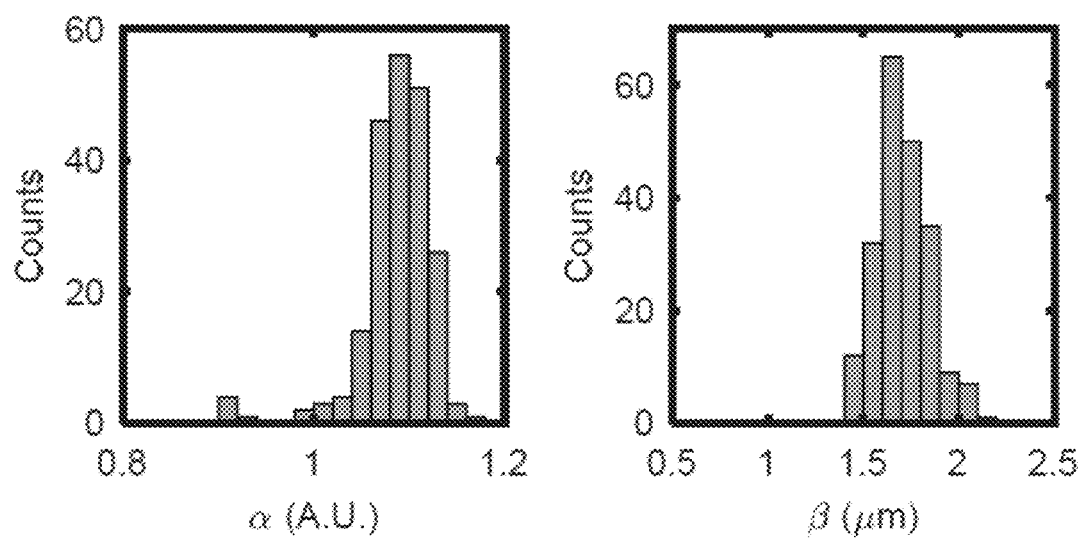
FIG. 12 shows exponential decay statistics of unreinforced HA brushes on spherical particles (eight micron diameter); $\alpha=1.09\pm0.04$ and $\beta=1.71\pm0.14$ µm where $N_{beads}=112$, $N_{profiles}=211$. The average R-square value from the fits is 0.988+/−0.005.
Figure 13:
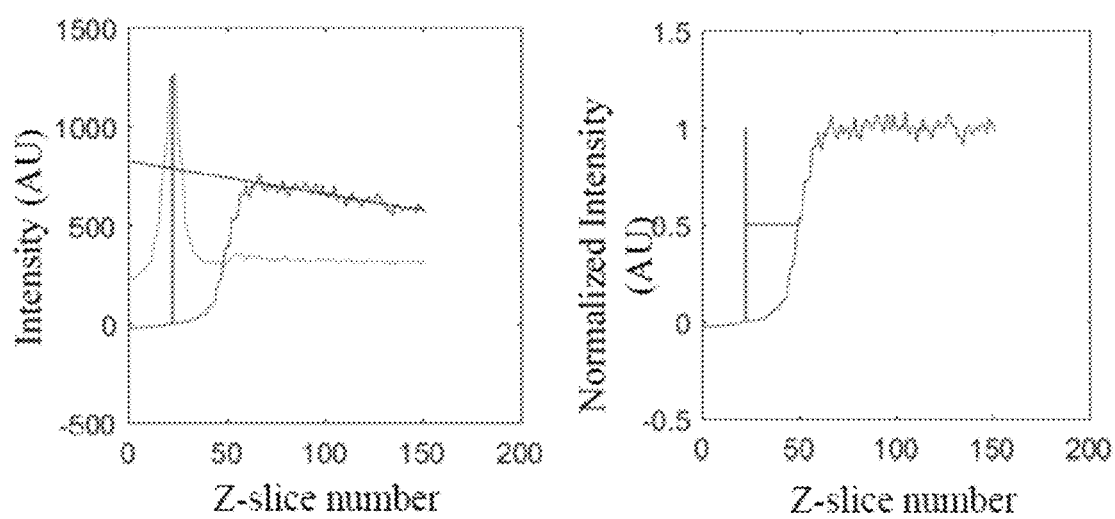
FIG. 13 (Left) shows intensity profiles of green (20 nm) and red (200 nm) beads interacting with planar HA brush. The black vertical line denotes the surface and the blue line is the linear fit of the intensity decay in the red beads (Right).
Figure 14:
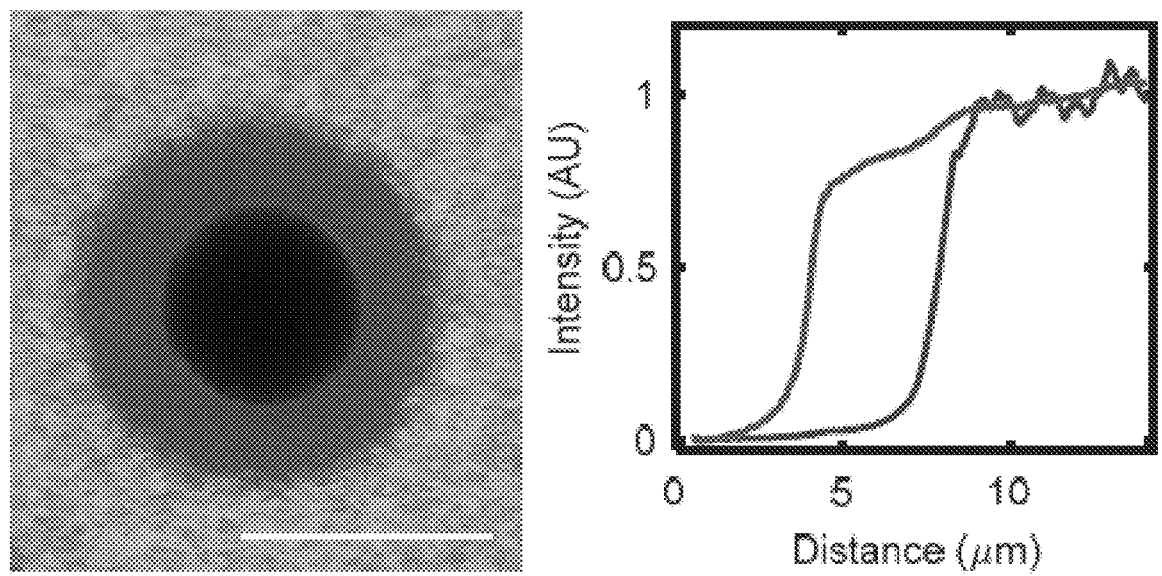
FIG. 14 (Left) shows 100 nm particle penetration particle exclusion assays (scale bar 10 µm) and (Right) profiles of particle penetration (red) and dextran (cyan, 10 kDa).

A. Fluorescent HA Brush Concentration Profile Statistics:

To characterize the shape of the brush concentration profiles, normalized fluorescent (GFPn) profiles in the brush region (defined as from microsphere surface to edge of brush) of spherical brushes were fitted with $\alpha \exp[-r/\beta]$ where r is distance to the surface of the microsphere (in the least square sense). Here, alpha is unitless. FIG. 12 shows exponential decay statistics of unreinforced HA brushes on spherical particles (eight micron diameter); $\alpha=1.09\pm0.04$ and $\beta=1.71\pm0.14$ µm where $N_{beads}=112$, $N_{profiles}=211$. The average R-square value from the fits is 0.988+/−0.005. FIG. 13 shows the typical values for unreinforced brushes on microspheres. FIG. 14 shows the distribution of values for the reinforced brushes on microspheres. In both cases, the brushes were grown for 4 hours at 30° C. Specifically, FIG. 13 (Left) shows intensity profiles of green (20 nm) and red (200 nm) beads interacting with planar HA brush. The black vertical line denotes the surface and the blue line is the linear fit of the intensity decay in the red beads. (Right) The normalized red bead intensity is plotted along with the same black vertical line denoting the surface. The difference in the number of slices in the zstack between the black vertical line and the 50% intensity value in the red bead plot is used to determine the thickness of the brush. FIG. 14 (Left) shows 100 nm particle penetration particle exclusion assays (scale bar 10 µm) and (Right) profiles of particle penetration (red) and dextran (cyan, 10 kDa). The penetration of 100 nm is less sharp than the 200 nm particles; however, they still remain roughly at the edge of the brush. The thickness of the spherical brush as measured with 100 nm particles is 3.4±0.2 µm (N=52), whereas the thickness when measured with 200 nm particles is 3.8±0.3 µm (N=148).

B. Particle Exclusion Assay Image Analysis, Brush Height Extraction for Planar Surfaces:

FluoSpheres (Molecular Probes, Inc, Carboxylate-Modified) were added to a final concentration of 0.007% w/v (green, 20 nm (Catalog number: F8787) and 0.7% w/v red, 200 nm (Catalog number: F8810). Optical characterization of the brush was made using a confocal image on a scanning laser confocal microscope (FV1000, Olympus, Tokyo, Japan; Objective: PlanApo N, 60×/1.42 NA oil) for high-resolution confocal images. When imaging planar polymer brushes, we use a 100 nm vertical step. A 20 µm thick z-stack is taken of the planar brush. The intensity profiles of the green and red beads are plotted (FIG. 13). The green profile corresponding to the smaller beads (20 nm) peaks at the surface of the sample. The red profile requires a linear fit of the intensity decay at high z positions above the object to correct for aberrations and absorption. The red profile is then corrected using this linear decay by normalization. The z-location of the 50% intensity value of the red profile is taken to be the average edge of the brush. Finally, the difference in the number of z-slices from the z-stack of the peak location of the green profile (the surface) and the 50% intensity value in the red profile (the average edge of the brush) is the thickness. Then, given that the z-stack is taken in 100 nm thick steps, one can convert the number of slices to a brush thickness value in microns.

Example 11

Stimulus Response and Reversibility to Ionic Strength

Figure 15:
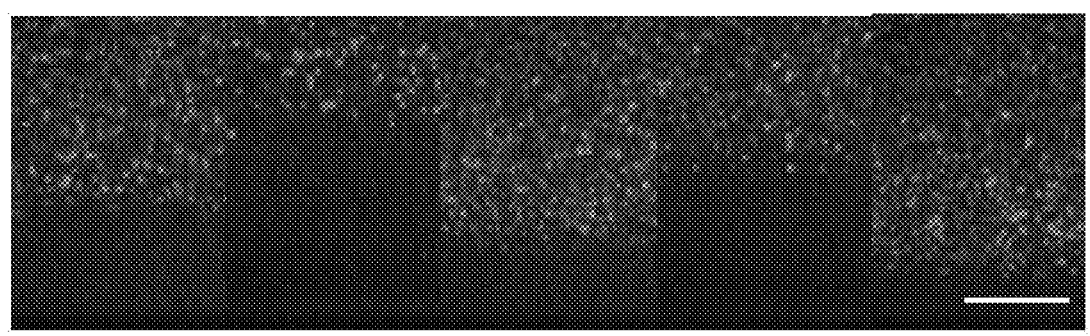
FIG. 15 illustrates the stimulus response and reversibility of the brushes to changing ionic strength. (A) Brush height during a series of solvent swaps from 130 mM to 1.3 mM for a brush previously grown for 16 hours (scale bar, 10 µm). (B) Quantification of the brush height shows that at ultra-low ionic strengths, the brush stretches out by nearly 200%, peaking at 22±2.5 µm during the first exchange.
Figure 15:
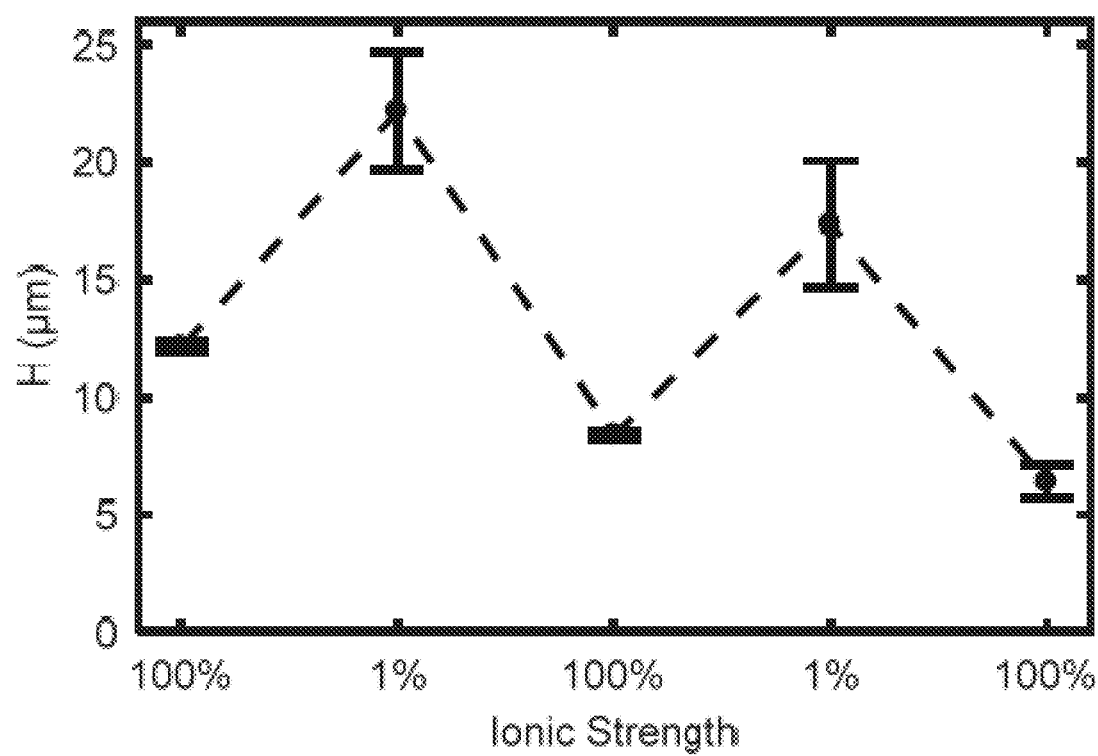
Figure 16:
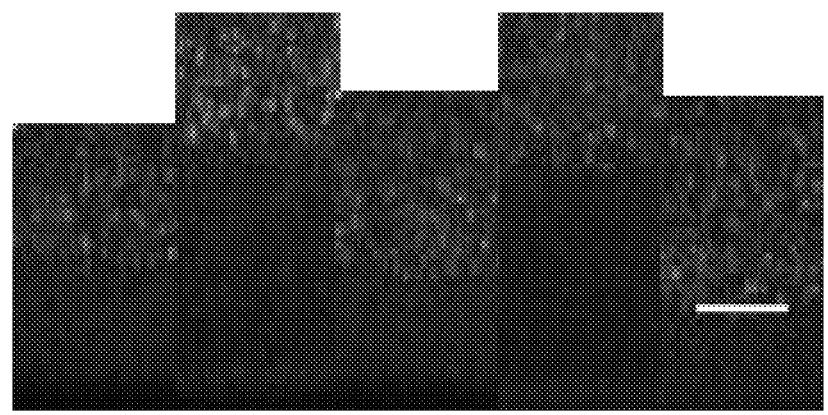
FIG. 16 illustrates the stimulus response and reversibility of the brushes to changing ionic strength. (A) Brush height during a series of solvent swaps from 130 mM to 1.3 mM for a brush previously grown for 4 hours (scale bar, 10 µm). (B) Height measurements from (A) for 5 regions of the sample (region area was 211×211 µm$^2$).
Figure 16:
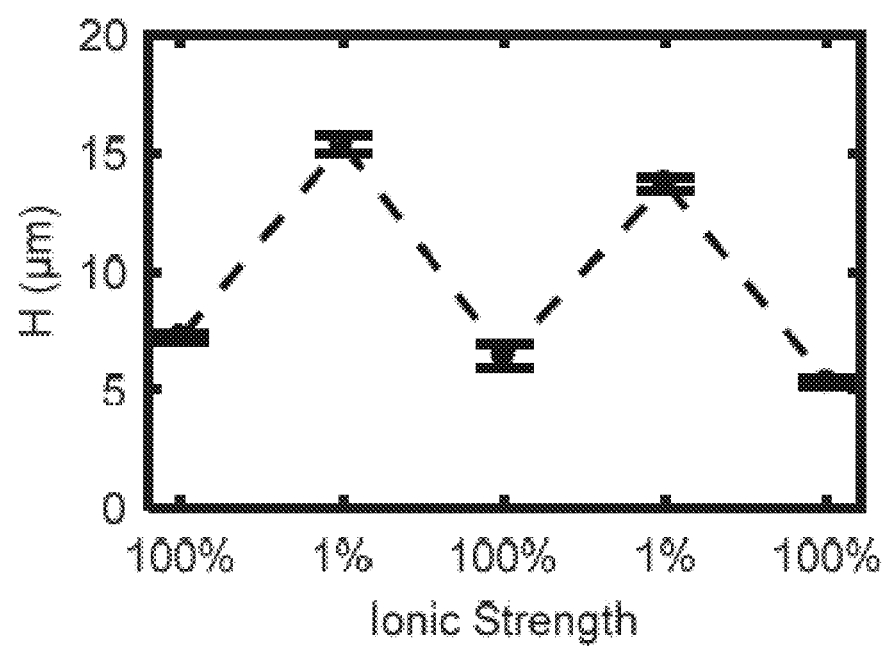

In this example, a sample was first imaged to establish a baseline height for the brush (using 200 nm particles) in the standard imaging buffer (40 µL activation buffer and 144, quenching buffer) which has an estimated total ionic strength of ~130 mM. The media was then exchanged three times with a 1% activation buffer diluted with ultrapure water, removing all liquid with each final wash. To image again, the 200 nm FluoSpheres were added to the sample, along with the typical volumes of activation buffer (40 µL) and quenching buffer (14 µL), but at 1% concentration diluted with ultrapure water to make the ionic strength 1.3 mM. To switch back to the normal imaging solution (130 mM), the media was exchanged three times with a 100% imaging buffer, undiluted. This process was repeated once more to study the reversibility of the brush height vs time. FIG. 15 illustrates the stimulus response and reversibility of the brushes to changing ionic strength. (A) Brush height during a series of solvent swaps from 130 mM to 1.3 mM for a brush previously grown for 16 hours (scale bar, 10 µm). (B) Quantification of the brush height shows that at ultra-low ionic strengths, the brush stretches out by nearly 200%, peaking at 22±2.5 µm during the first exchange. While the brush swelling and shrinking is reversible, the repeated handling (and tension induced by stretching) leads to some loss of the HA, which is weakly bound to the HA synthase. As a consequence, a gradual decrease in the overall brush height is observed. Each data point corresponds to five independent measurements. FIG. 16 (A) illustrates the stimulus response and reversibility of the brushes to changing ionic strength, switching from 100% to 1% dilution of the imaging buffer with deionized water. The ionic strength was diluted from ~130 mM to ~1.3 mM. In contrast to the example displayed in FIG. 15, this shorter brush ($t_{growth}$=4 hrs rather than $t_{growth}$=15 hours) stretches only to ~15 μm (from ~7 μm) rather than 22 μm; but it also is more reversible, losing less height with each solvent swap (scale bar 10 microns). (B) Height measurements from (A) for 5 regions of the sample (region area was 211×211 μm²).

Example 12

Pipetting Controls

Figure 17:
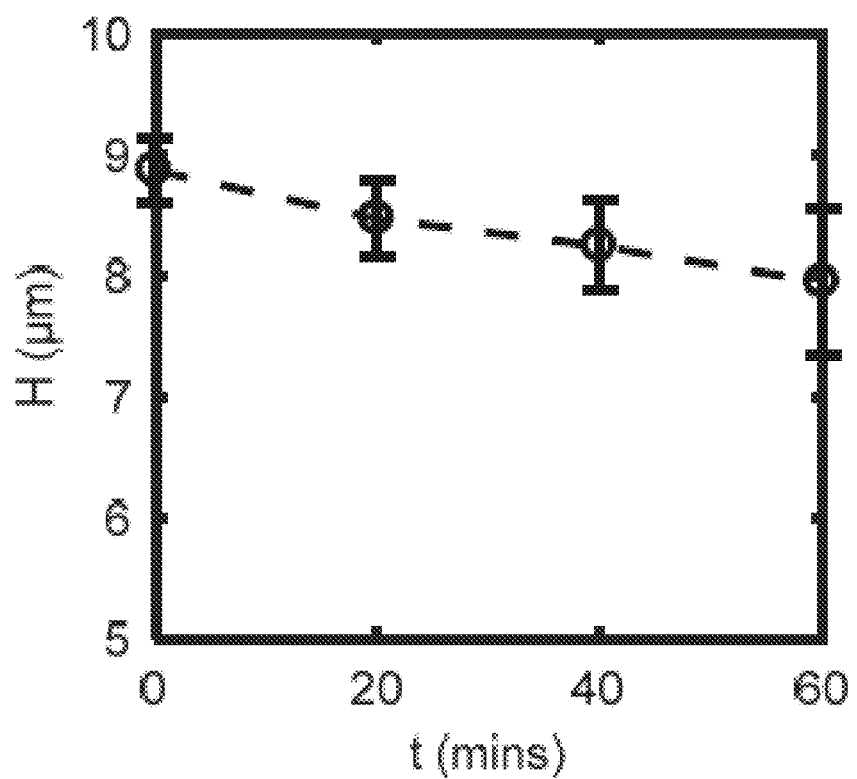
FIG. 17 illustrates the average height of planar brushes subjected to 18 gentle pipetting pump actions over 1 hour at 30° C.

In this example, samples were exposed to pipetting to examine the impact on the brush thickness (loss of HA). Since the HA is not permanently bound to the HA synthase, some HA loss is expected. Post HA growth, the synthesis was quenched and the height was determined using 200 nm beads. Then, the solution in the sample was mixed by pipetting the sample gently where the solution is pulled up and down into the pipette tip, six times at 30° C. The sample was then imaged again to determine the brush height. The solution was then pipette mixed again six times in the same manner. Then, imaged again. This process was repeated until the sample had endured 3 rounds of mixing, totaling 18 gentle pipette pumps. The effect was to mimic conditions of exchanging solvents. As shown in FIG. 17, over the course of one hour and 18 gentle pipette pump actions, the average height of the planar brushes was relatively stable, showing a decrease in average values, but overlapping standard deviations.

Example 13

HA Brush Decay Assay

To measure the short term decay of planar brushes: Post HA growth, the synthesis was quenched and the sample was imaged using the methods described previously in the presence of a stage-top incubator to maintain the temperature at 30° C. (130 mM, $t_{growth}$=4 hrs). After imaging, the sample was allowed sit, undisturbed and then measured every 20 minutes. Long term decay: for one year, microsphere samples were stored at in the dark at room temperature in the same buffer in which they are imaged. Mineral oil was added to the surface of the buffer to hinder evaporation. Each spherical brush height measurement was performed using a fresh sample under normal imaging conditions (room temp, 150 mM).

Example 14

On Demand Synthesis: Pausing and Restarting HA Brush Growth

The sample was washed three times with a mixture of the activation buffer (but with no UDP-sugars) and the quenching buffer in a ratio of 3:1, respectively. After replacing the volume with this mixture, the sample was allowed to sit, HA growth paused, for 30 mins in the 30° C. incubator. The sample was then washed with the activation buffer three times. After replacing the volume with the activation buffer, the UDP-sugars were added to a final concentration of 5 mM and growth was allowed to proceed again.

Example 15

Hyaluronidase Treatment

To digest the HA brush, 0.5 units of bacterial hyaluronidase (from *Streptomyces hyalurolyticus*, Sigma-Aldrich H1136) or 20 units of bovine hyaluronidase (from bovine testes Type I-S, Sigma-Aldrich H3506) was added to 80 μL samples. In experiments where HA synthesis was desired (post hyaluronidase digestion), 8 mg/mL bovine serum albumin (BSA) was added to the sample and incubated for 40 mins at 30° C. prior to UDP-sugar addition to block the non-specific binding of hyaluronidase which can interfere with regeneration. Controls were performed to ensure that the HA is fully removed with these treatments.

Example 16

Brush Regeneration

Figure 18:
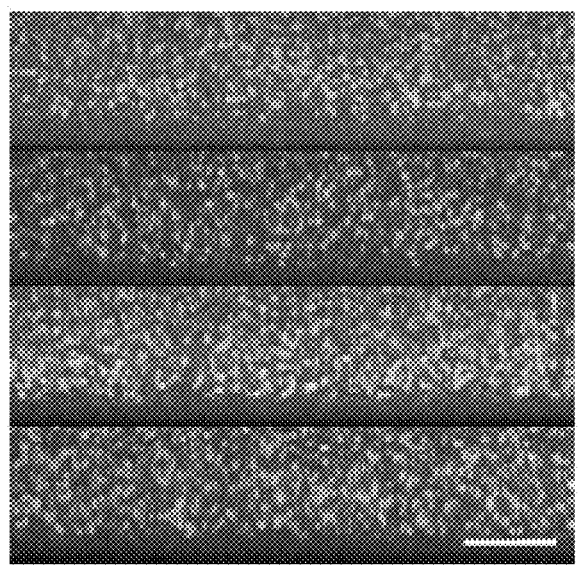
FIG. 18 illustrates (A) Regeneration of HA brush after enzymatic degradation with hyaluronidase. Top image shows brush after one hour of growth before digestion. The next three images show the regenerated brush following digestion and one hour regrowth 1, 2, and 3 times (130 mM, scale bar 10 µm). (B) Brush height versus the number of regeneration times. (C) Interrupted growth (point A) followed by an additional growth period of one hour (point B). (D) Brush stability versus time (unreinforced, natural brush, 130 mM, $t_{growth}=4$ hrs).
Figure 18:
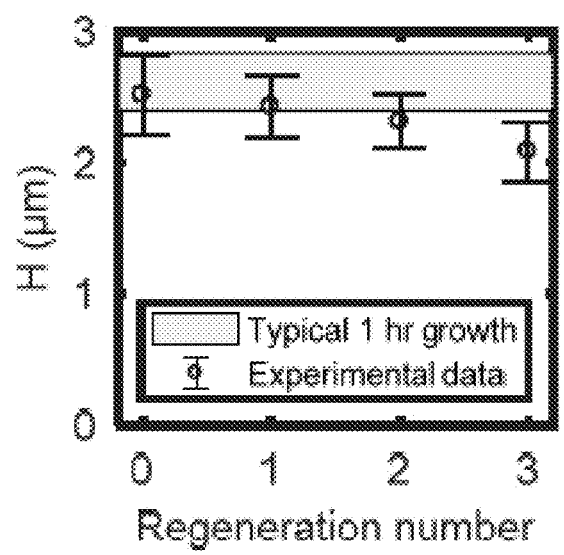
Figure 18:
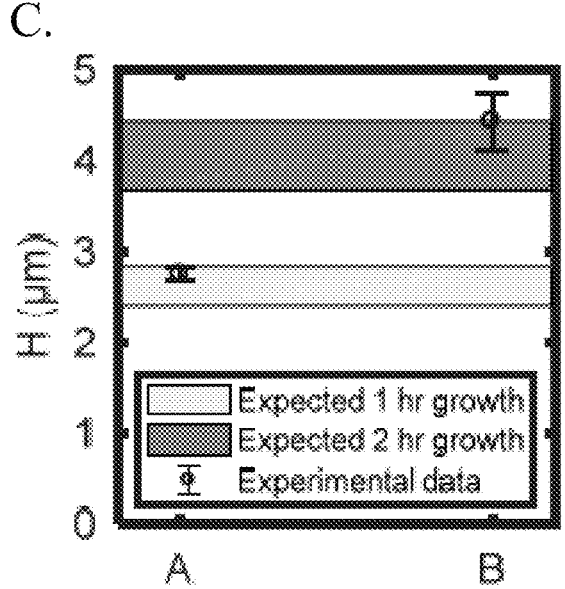
Figure 18:
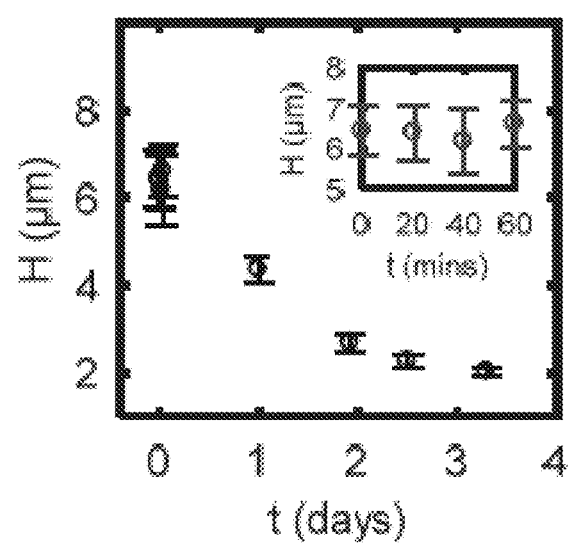

After exchanging the Tris storage media for activation buffer, the sample was incubated with 2% BSA (SeraCare 1900-0016) in PBS to a final concentration of 1% for 20 mins in the 30° C. incubator. HA synthesis was then activated and the sample was allowed to grow for the desired time. 0.5 units/μL bovine hyaluronidase dissolved in PBS was added to the sample to a final concentration of 0.025 units/μL and allowed to sit in the 30° C. incubator for 30 mins. The hyaluronidase was washed away by rinsing the sample with the activation buffer 20 times, ensuring to remove all the liquid with each wash. HA synthesis was then reactivated and allowed to proceed for the desired time. Hyaluronidase addition and removal (followed by a growth period of 1 hr) was repeated three times. The height was measured and averaged over five areas of the sample, each 211×211 μm². FIG. 18 illustrates (A) Regeneration of HA brush after enzymatic degradation with hyaluronidase. Top image shows brush after one hour of growth before digestion. The next three images show the regenerated brush following digestion and one hour regrowth 1, 2, and 3 times (130 mM, scale bar 10 μm). (B) Brush height versus the number of regeneration times. (C) Interrupted growth (point A) followed by an additional growth period of one hour (point B). (D) Brush stability versus time (unreinforced, natural brush, 130 mM, $t_{growth}$=4 hrs).

Example 17

Surface Reinforcement of the HA Brush

In order to form covalent bonds between the HA polymers and the grafting surface, carbodiimide conjugation was used to crosslink the carboxyl groups on HA to the primary amine groups ($-NH_2$) on the grafting surface. At the end of HA synthesis, solution was exchanged with pH 7.0, 75 mM $NaKPO_4$, 50 mM NaCl. For this protocol, no DTT was added to the buffer because DTT reacts with EDC. Next, 100 mM EDC (1-Ethyl-3-(3 dimethylaminopropyl) carbodiimide, Sigma E1769) and 50 mM sulfo-NHS (sulfo-Nhydroxysuccinimide, Sigma-Aldrich 56485) was added to the sample. After 30 min, the solution was exchanged with newly dissolved EDC and sulfo-NHS (repeated twice). The sample was left overnight at room temperature. The next day, the solution was exchanged with a pH 8.0, 50 mM borate buffer (2 hrs) to quench the crosslinking reaction. Last, the reinforced brush was washed extensively with PBS.

Figure 19:
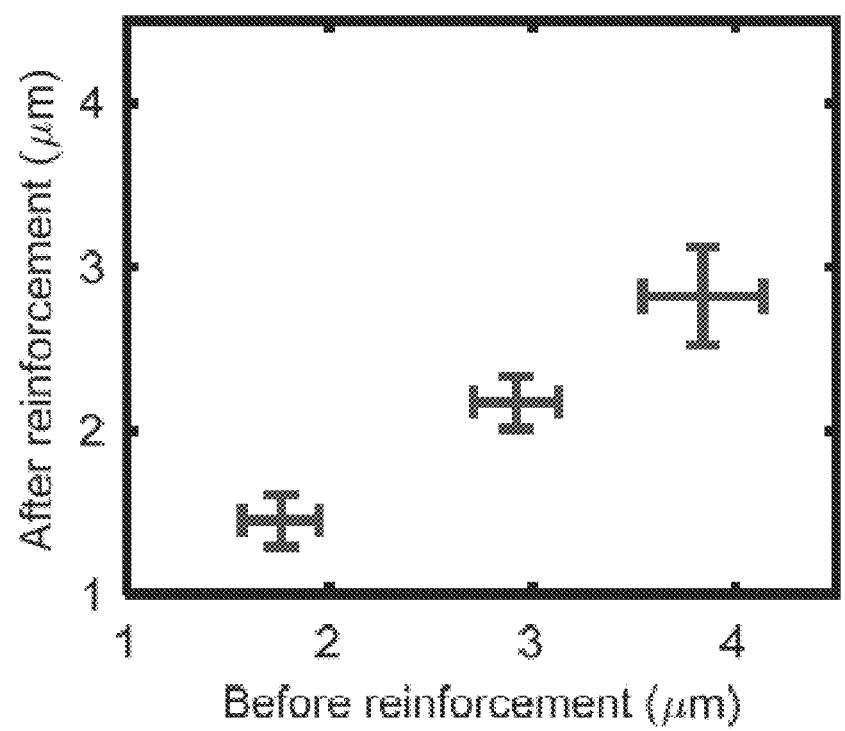
FIG. 19 shows brush thickness before and after reinforcement. The slope of a line drawn through the data is 0.66.

FIG. 19 shows brush thickness before and after reinforcement. The slope of a line drawn through the data is 0.66. As shown in FIG. 19, reinforcing the brush by covalent binding to the interface reduces the brush height by about 66% on average.

Figure 20:
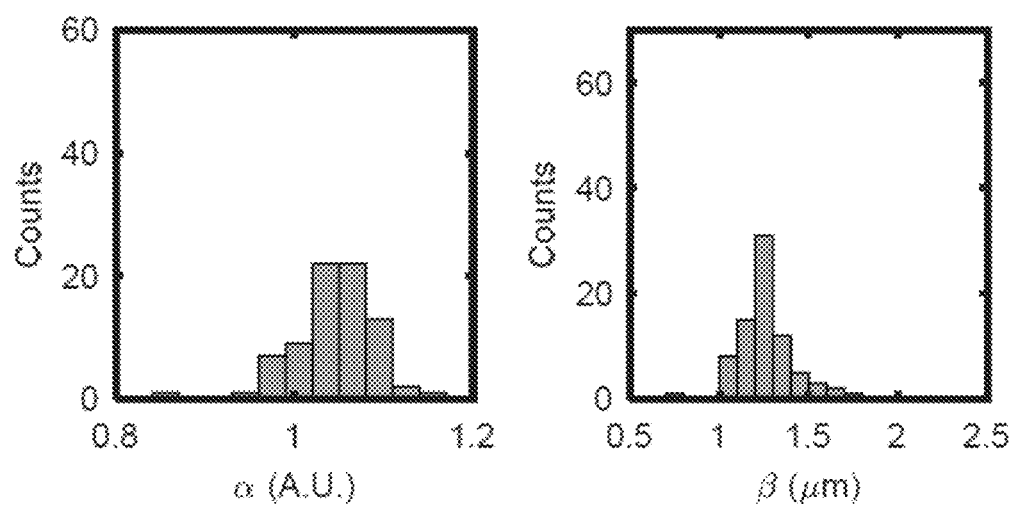
FIG. 20 shows exponential decay statistics of reinforced HA brushes on spherical particles (eight µm diameter) measured by fluorescent labeling with GFPn; $\alpha=1.04\pm0.05$ and $\beta=1.26\pm0.15$ µm where $N_{beads}=81$, $N_{profiles}=360$. The average R-square value from the fits is 0.992±0.009.

FIG. 20 shows exponential decay statistics of reinforced HA brushes on spherical particles (eight μm diameter) measured by fluorescent labeling with GFPn; $\alpha=1.04\pm0.05$ and $\beta=1.26\pm0.15$ μm where $N_{beads}=81$, $N_{profiles}=360$. The average R-square value from the fits is $0.992\pm0.009$.

Figure 21:
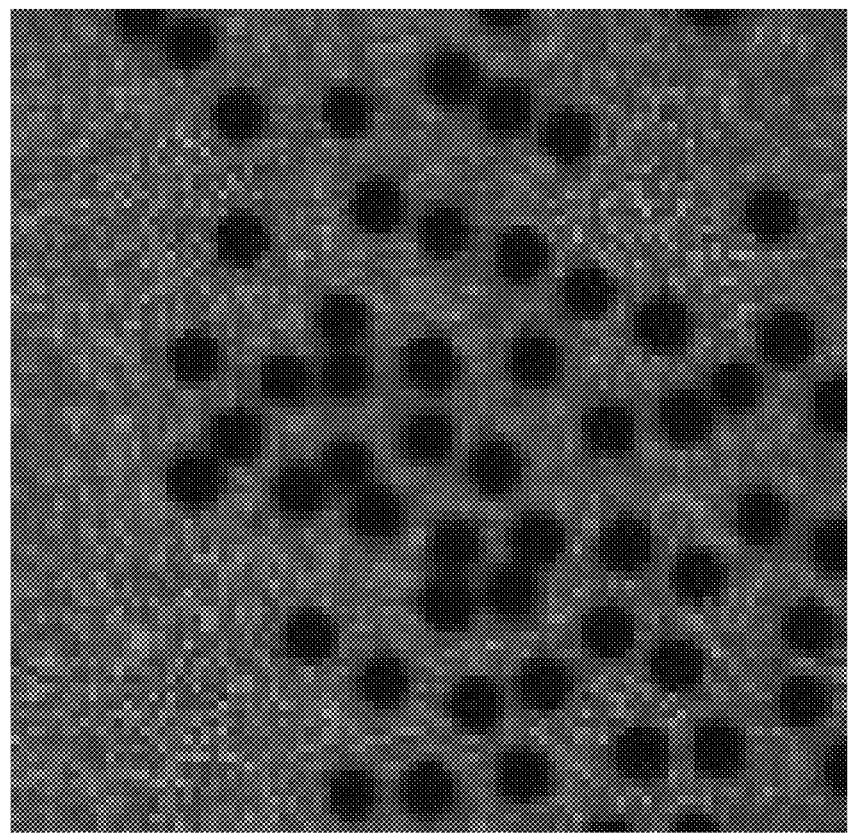
FIG. 21 shows reinforced brushes on spherical particles treated with hyaluronidase.

As shown in FIG. 21, reinforced brushes on spherical particles are still digested by hyaluronidase, indicating minimal HA-HA crosslinking within the brush.

Example 18

Bacterial Fragment Removal with Detergent

In this example, detergent sodium dodecyl sulfate (SDS, Sigma-Aldrich L6026, 1 mg/mL) was used to destroy the membrane fragments, including the embedded HA synthase in order to demonstrate that reinforced brushes are bound to the underlying surface; whereas in comparison non-reinforced brushes are destroyed along with the membranes.

Example 19

Laser Micropatterning of HA Synthase Activity

This example describes a method of laser micropatterning HA synthase activity.

After exchanging the Tris storage media for activation buffer, in order to define the surface, a low concentration of 8 μm silica microspheres were added to the sample and brought into focus with diffraction interference contrast (DIC) microscopy on the confocal microscope (within a stage-top temperature incubator at 30° C. incubator and a wet sponge to maintain humidity). Then, the focus was adjusted to be below the center of the microspheres an amount equal to the radius such that the focus should now be on the surface of the sample, rather than at the center of the spheres. This method allows one to focus at the plane of the membrane fragments containing HAS without introducing other chemistries or fluorescence. Then, the confocal microscope's 405 nm laser was scanned in a predetermined area using optimized settings to eliminate HA synthase activity. Applicants found that treating the surface with an energy density greater than $2.13E-04$ $J/\mu m^2$ was sufficient. When applying the laser to a new area, we first refocused on the surface using the microspheres as a reference. After all desired areas were laser treated, we activated HA synthesis and allowed the sample to grow for the desired time.

Figure 22:
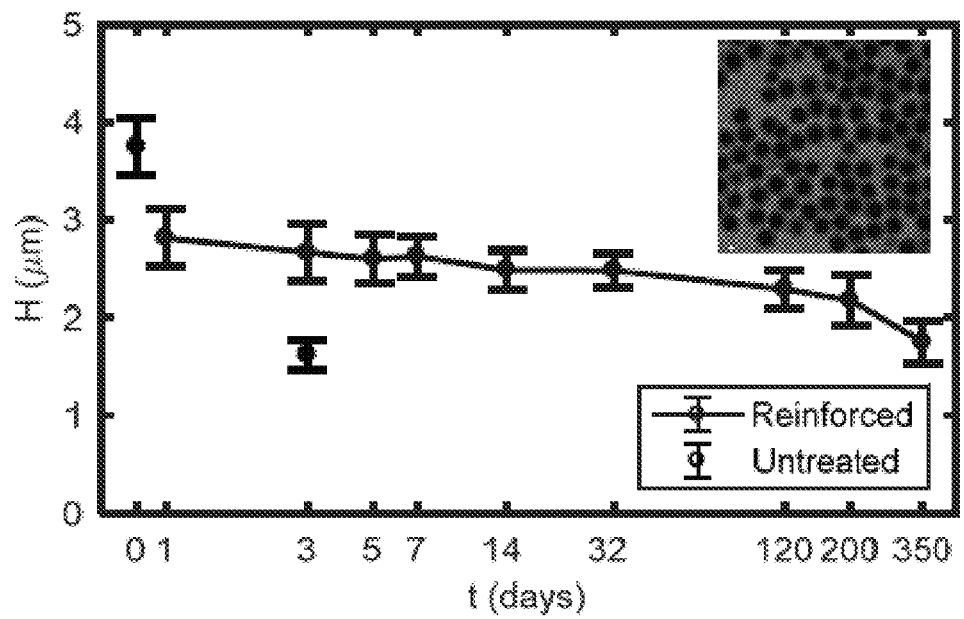
FIG. 22 illustrates stabilization and micropatterning of HA brushes. (A) HA brushes can be stabilized via chemical crosslinking to the substrate. The reinforced brushes on spherical particles remain intact for over one year as determined by periodic measurements of brush height. Non-reinforced brushes decay in a few days. (B) Reinforced brushes on spherical particles resist detergent treatment (SDS) despite the removal of membrane fragments. (C) UV micropatterning of HA synthase activity with a confocal microscope ($\lambda=405$ nm). (D) Checkerboard pattern illustrating binary patterning of the brush. Red regions indicate areas where no brush grew; cyan regions indicate regions where brush expels red nanoparticles. Top: XZ confocal side view of micropatterned brush. Bottom: XY confocal image taken at the glass interface. All data in this figure were acquired in physiological conditions (130 mM, $t_{growth}=4$ hrs). Scale bars, 10 µm.
Figure 22:
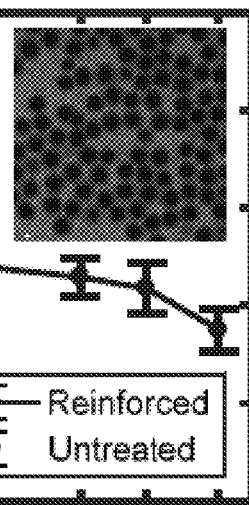
Figure 22:
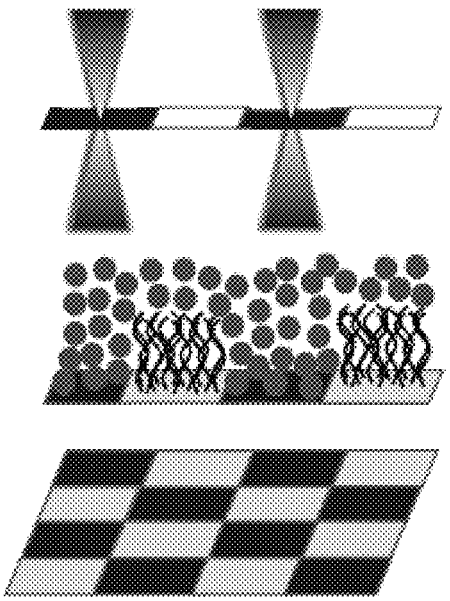
Figure 22:
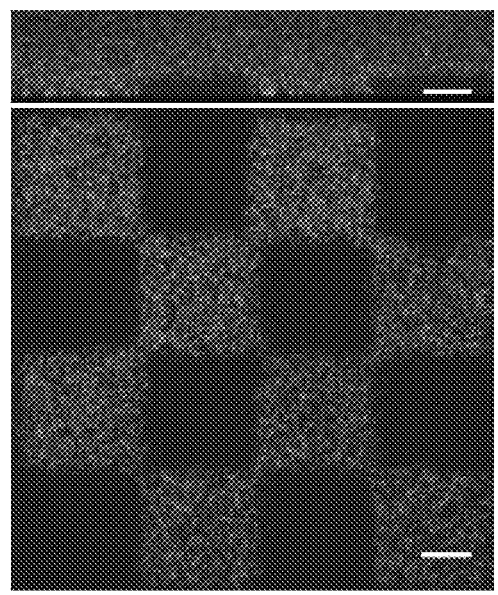

FIG. 22 illustrates stabilization and micropatterning of HA brushes. (A) HA brushes can be stabilized via chemical crosslinking to the substrate. The reinforced brushes on spherical particles remain intact for over one year as determined by periodic measurements of brush height. Non-reinforced brushes decay in a few days. (B) Reinforced brushes on spherical particles resist detergent treatment (SDS) despite the removal of membrane fragments. This confirms the HA is stably bound to the underlying glass substrate. (C) UV micropatterning of HA synthase activity with a confocal microscope ($\lambda=405$ nm). (D) Checkerboard pattern illustrating binary patterning of the brush. Red regions indicate areas where no brush grew; cyan regions indicate regions where brush expels red nanoparticles. Top: XZ confocal side view of micropatterned brush. Bottom: XY confocal image taken at the glass interface. All data in this figure were acquired in physiological conditions (130 mM, $t_{growth}=4$ hrs). Scale bars, 10 μm.

Example 20

Mouse Embryonic Fibroblast Interaction with Reinforced Planar Brushes

Mouse embryonic fibroblasts (MEF) modified to express fluorescent (green) vinculin were used to study how cells interact with reinforced HA brushes generated by HA synthase. The cells were cultured in Dulbecco's Modified Eagle's Medium (D-MEM) supplemented by 10% FBS (fetal bovine serum, Corning CellGro: 35-010-CV), 1% penicillin and 4 mM L-glutamine. Brushes were grown for 8 hours and then reinforced to avoid decay over the length of the 12 hour experiment. The reinforced brushes were covered with cell culture media and then seeded with MEF cells. Time lapse videos were made using DIC imaging for 12 hours using a 40× Nikon Plan Fluor oil lens on a Nikon TE2000. Fluorescent images of the vinculin-rich focal adhesions were acquired using confocal microscopy after overnight seeding of the MEF cells.

Figure 23:
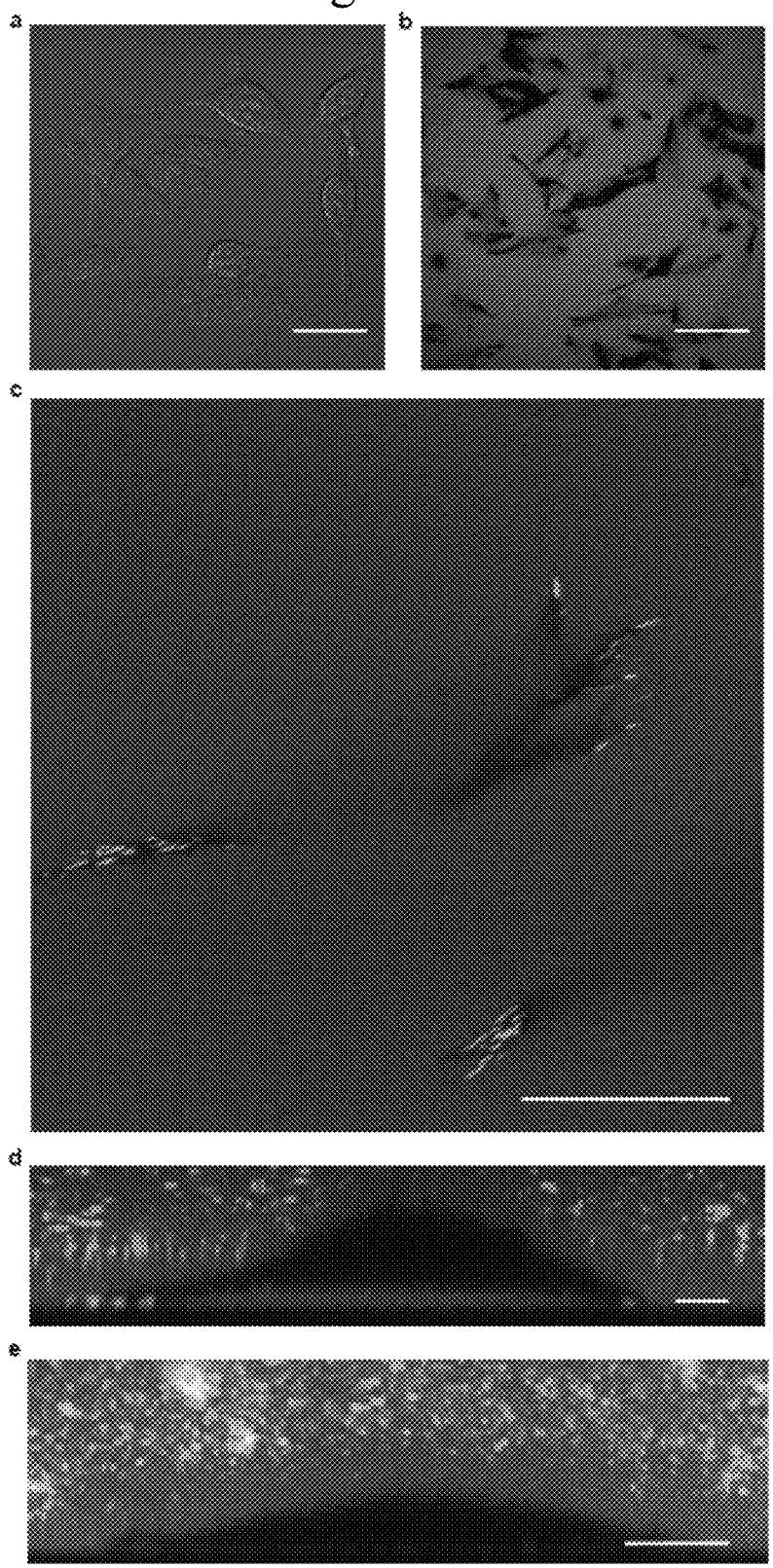
FIG. 23 illustrates fibroblast interactions with the HA brush. (A) Fibroblasts locally digest the HA brush and adhere to the underlying glass interface. Scale bar 25 µm. (B) Fluorescent dextran (cyan) highlights space under adherent cells. Black regions correspond to cell area in direct contact with surface. Scale bar 50 µm. (C) Fibroblasts attach to the interface underlying the HA brush, expressing mature focal adhesions (green, vinculin). Dextran is apparent underneath the spread cell. Scale bar 20 µm. (D) z-slice of the same adherent fibroblast from (C) sitting on a cushion of HA. Scale bar 10 µm. (E) Particle exclusion assay reveals mouse embryonic fibroblasts express a thick glycocalyx. All mouse embryonic fibroblast images were taken after 12 hours exposure to the HA reinforced brush. Scale bar 10 µm.

FIG. 23 illustrates fibroblast interactions with the HA brush. (A) Fibroblasts locally digest the HA brush and adhere to the underlying glass interface. Scale bar 25 μm. (B) Fluorescent dextran (cyan) highlights space under adherent cells. Black regions correspond to cell area in direct contact with surface. Scale bar 50 μm. (C) Fibroblasts attach to the interface underlying the HA brush, expressing mature focal adhesions (green, vinculin). Dextran is apparent underneath the spread cell. Scale bar 20 μm. (D) z-slice of the same adherent fibroblast from (C) sitting on a cushion of HA. Scale bar 10 μm. (E) Particle exclusion assay reveals MEFs express a thick glycocalyx. All MEF images were taken after 12 hours exposure to the HA reinforced brush. Scale bar 10 μm.

Example 21

HA Film Preparation

Rooster comb HA (Thomas Scientific H5388, MW range $5.0\times10^5$-$1.2\times10^6$ Da) was fluorescently labeled with Alexa 546 (ThermoFisher Scientific A20002) using established protocols (Pouyani, T., et al., Functionalized Derivatives of Hyaluronic Acid Oligosaccharides: Drug Carriers and Novel Biomaterials. Bioconjugate Chemistry 1994, 5(4): 338-347). Briefly, the HA was dissolved in water and mixed with a 20-40 fold molar excess of dihydrazide and pH balanced to 4.75. A 4M excess of EDC was dissolved in water and added to the HA solution and the pH was maintained at 4.75 by addition of HCl over the course of 2 hrs. Next, using NaOH, the pH was balanced to 7 and the HA was precipitated with chilled ethanol. To achieve 1 dye molecule per 50 nm HA, we added dye at a final concentration of 0.1 mg/mL with 2 mg/mL of the dihydrazide-modified HA. To remove unbound dye, the solution was dialyzed with ultrapure water for 1 week, refreshing the water every day. The HA film was deposited on glass coverslips that were sonicated in ultrapure water and acetone, then plasma cleaned. The slides were then covered with 50 pg/mL of the fluorescent HA and allowed to sit in the 4° C. refrigerator overnight with wet sponges to minimize evaporation. In the morning, the slides were rinsed with DI water, dried with nitrogen, and mounted in teflon sample holders.

Example 22

Pseudomonas Aeruginosa Bacterial Culture

A GFP-producing strain of *Pseudomonas aeruginosa* PAO1 was streaked on a lysogeny broth (LB) (Teknova L9130) agar plate incubated at 37° C. A single bacterial colony from the agar plate was inoculated into 5 mL of LB broth and grown overnight in a shaking incubator (160 rpm, 37° C.). 100 μL of the overnight culture was inoculated into 5 mL of fresh LB broth under similar conditions until the optical density (OD) had a value of 1. This bacterial culture was then diluted to a value of OD 0.02 and used for inoculating the hyaluronan film and brush samples.

Example 23

Biofilm Growth on HA Brush

Post hyaluronan growth, the synthesis was quenched and the brushes were reinforced to create stable structures. The EDC/sulfo-NHS buffer that was used to reinforce the brush overnight was replaced with borate buffer for 2 hours, which was then replaced with fresh borate buffer and allowed to sit overnight at 4° C. This was followed by two PBS buffer exchanges, each for one hour at room temperature. 100 μL of the OD 0.02 culture was then added to the sample and incubated at 37° C. For the one-day experiments, the samples were imaged with confocal microscopy before bacteria removal. After imaging, the sample was washed in a manner where the solution was pulled up and down into the pipette three times, and for two rounds, and this procedure was repeated twice with fresh LB broth both times. The washed samples were topped with fresh LB and imaged again to check for bacterial adherence and biofilm formation. 20 nm fluorescent beads were gently added and imaged to locate the coverslip surface. For the five day experiments, the samples were replenished with fresh LB broth every 24 hours and on the fifth day, the brushes were imaged using the procedure described above.

Example 24

Bacteria Growth on HA Films and Glass Substrates

Post HA film preparation, 100 μL of the OD 0.02 culture was added to the sample and incubated at 37° C. The sample area of the HA brush, HA film and glass was the same size for all cases. Imaging pre and postwash and the washing steps are identical to that for the biofilm.

Figure 24:
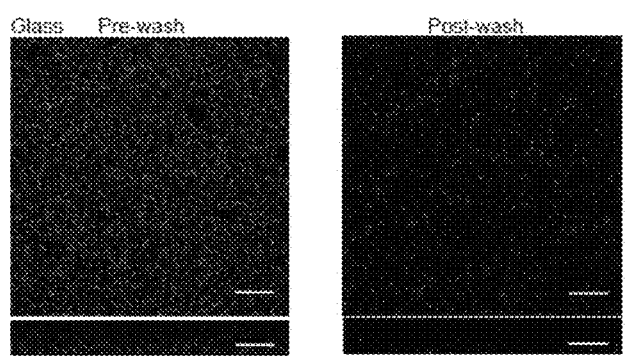
FIG. 24 shows confocal micrographs of GFP-producing *Pseudomonas aeruginosa* (PAO1) interacting with a glass interface (A), a HA film (B), and a reinforced HA brush (C). Left: biofilm growth before washing (1 day, pre-wash). Right: biofilm growth after washing (1 day, post-wash). Dextran was used to identify the glass interface beneath the brush. XZ side views of the biofilms are presented below each respective XY top view of the samples. Scale bars, 30 µm. (D) Comparison of the relative percentage of adherent bacterial volume before and after washing the glass, film and brush interfaces. Data were taken in triplicates and averaged over 5 regions per sample.
Figure 24:
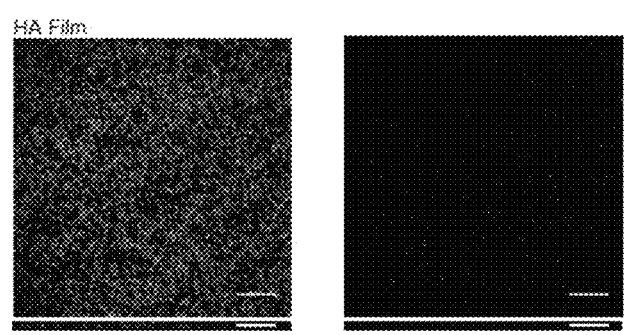
Figure 24:
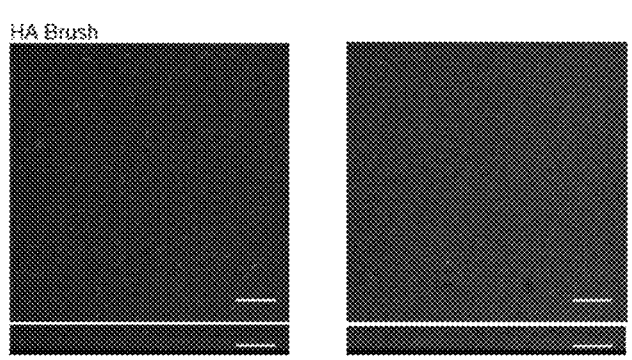
Figure 24:
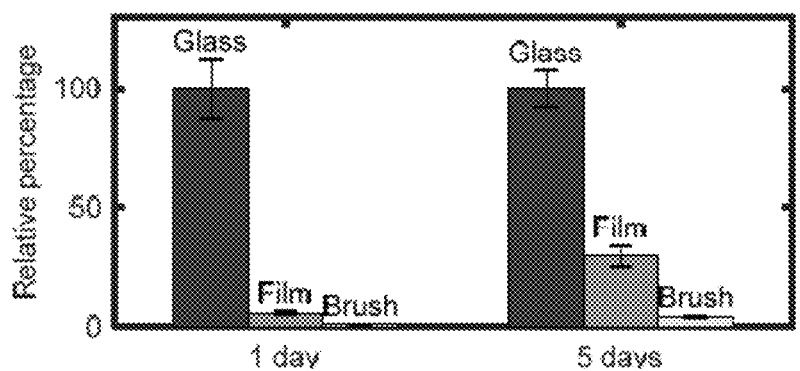

FIG. 24 shows confocal micrographs of GFP-producing *Pseudomonas aeruginosa* (PAO1) interacting with a glass interface (A), a HA film (B), and a reinforced HA brush (C). Left: biofilm growth before washing (1 day, pre-wash). Right: biofilm growth after washing (1 day, post-wash). Dextran was used to identify the glass interface beneath the brush. XZ side views of the biofilms are presented below each respective XY top view of the samples. Scale bars, 30 (D) Comparison of the relative percentage of adherent bacterial volume before and after washing the glass, film and brush interfaces. Data were taken in triplicates and averaged over 5 regions per sample.

Example 25

Bacteria Quantification

The total volume of living bacteria stuck to the surfaces in PAO1 biofilms after washing was quantified. Confocal microscopy was used to image a 3D volume. The total bacterial volume was determined for all samples by counting all voxels in the confocal z-stacks that had a signal that was above the noise threshold, indicating bacteria was present. Briefly: the 3D z-stacks were exported as .oib files in order to preserve the metadata and processed with Matlab through custom codes. The BioFormats package was used to for reading the images and defining the stack structure for further processing. Noise reduction was performed using high-pass filtering with a Gaussian filter and the images were further binarized using a suitable thresholding algorithm. The total volumes of live bacteria on the brushes, films and glass substrates were calculated by counting the non-zero voxels in the binarized image stack. The average live bacterial volume in the region with a depth of five microns above the brush, film, and glass surface was used in calculations.

The bacteria-biofilm interactions are summarized in Table 1. The top panel shows total average volume of PAO1 bacteria post-wash on glass, HA film and HA brush in a 211×211×5 μm$^3$ volume averaged over 5 measured areas. The bottom panel shows percentage PAO1 bacteria adherent to HA film and HA brush post-washing relative to the bacteria sticking to the glass.

TABLE 1

Bacteria-Biofilm Interactions.

| | μm$^3$ | Glass | Film | Brush |
|---|---|---|---|---|
| 1 day | Mean | 4106.9 | 246.7 | 39.2 |
| | SEM | 515.0069 | 30.1419 | 2.9142 |
| 5 days | Mean | 683.3 | 203.5 | 29.3 |
| | SEM | 52.9603 | 29.9655 | 2.3096 |

| | % (rel. glass) | Glass | Film | Brush |
|---|---|---|---|---|
| 1 day | Mean | 100 | 6.007 | 0.9552 |
| | SEM | | 12.54 | 0.7339 | 0.071 |
| 5 days | Mean | 100 | 29.7758 | 4.2897 |
| | SEM | | 7.7509 | 4.3856 | 0.338 |

Example 26

Characterization of GFP-Labeled HA Synthase Brush Interfaces

This example describes the characterization of HA synthase brushes labeled with green fluorescent protein (GFP).

GFPn (neurocan-G1 EGFP fusion protein) is expressed by HEK 293 EBNA cells, which are cultured at 37° C. and 5% $CO_2$ in DMEM/F12, with 10% FBS, 1% L-glutamine with 0.1% puromycin (EMD Biosciences, CA) (Ruths M, et al., 2000, Repulsive Forces and Relaxation on Compression of Entangled, Polydisperse Polystyrene Brushes, *Macromolecules* 33, 3860-3870.; Milner S T, 1991, Polymer brushes, *Science* (New York, N.Y.) 251, 905-914.). Cells are grown to confluence, at which time the serum is removed from culture media and the cells are then incubated for 48 hours under serum free conditions. 50 mL of conditioned media is collected from a total of 5 culture flasks and concentrated to ~2 mL by centrifugal ultrafiltration with a membrane cut-off of 30 kDa (Millipore, Mass.). The His-tagged fusion protein then is purified on a HisPur Cobalt spin column (Thermo Scientific, IL) and used for HA labeling in both live cell culture and tissues, as well as biomimetic HA synthase interfaces.

Figure 25:
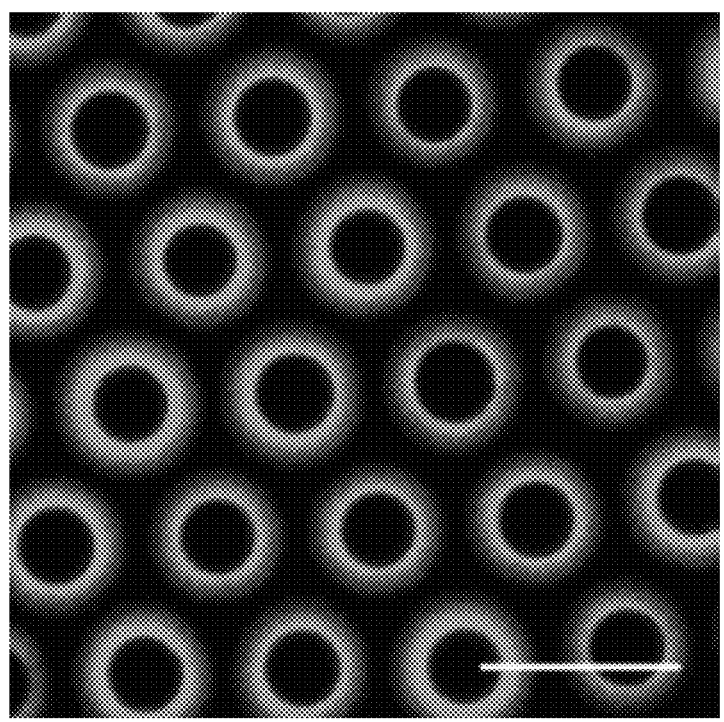
FIG. 25 shows HA synthase beads with HA brushes labeled with GFP.

HA synthase beads with HA brushes labeled with GFP are shown in FIG. 25 (scale is 20 µm).

Figure 26:
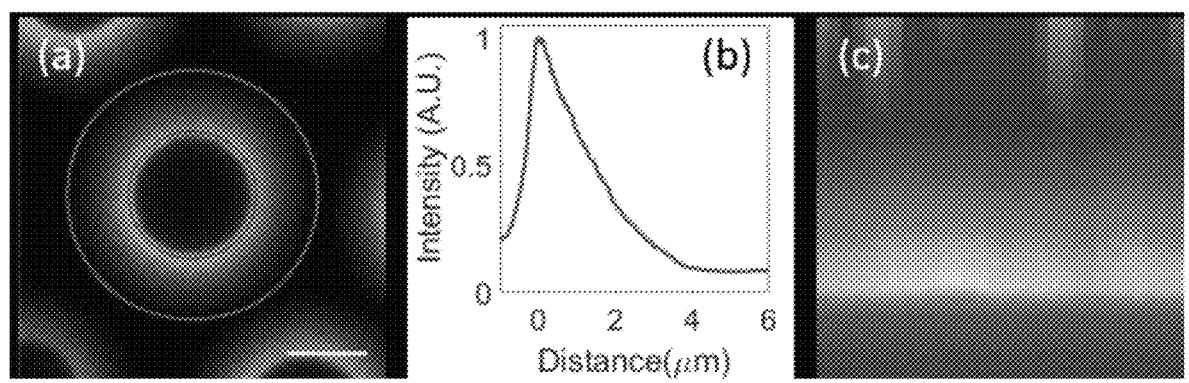
FIG. 26 illustrates the analysis of HA concentration profiles from the HA synthase sphere. (A) the middle of the bead from z-stack is shown. The profile is averaged over azimuthally to produce the result in (B). Variability in the concentration profile with azimuthal angle is shown in (C), where the x-axis is angle (0-360°) and y-axis is distance from bead.

FIG. 26 illustrates the analysis of HA concentration profiles from the HA synthase sphere. (A) care is taken to find the middle of the bead from z-stack. The profile is averaged over azimuthally to produce the result in (B). Variability in the concentration profile with azimuthal angle is shown in (C), where the x-axis is angle (0-360°) and y-axis is distance from bead.

A unique and convenient feature of the HA brushes is their huge extent. This makes optical measurement of the concentration profile feasible, as shown in the data in FIG. 25 and FIG. 26. Furthermore, access to GFPn, a dedicated hyaluronan-binding protein linked to GFP which selectively binds to HA, makes fluorescent characterization straightforward and less disruptive since it requires no chemistry that might alter the HA distribution nor the HA synthase performance. HA concentration profiles can be compared with theoretical predictions like the classic Witten-Milner-Cates parabolic prediction and examined to analyze brush heterogeneity (FIG. 26).

Example 27

Particle Exclusion Assay and Brush Penetration by Nanoparticles and Molecules

This example describes a particle exclusion assay used to visualize and characterize HA synthase brushes.

The traditional method to characterize the pericellular matrix (PCM) on cells is to use a crude assay based on fixed-red blood cells (RBC)(Evanko S. P. et al., 1999, Formation of Hyaluronan- and Versican-Rich Pericellular Matrix Is Required for Proliferation and Migration of Vascular Smooth Muscle Cells, *Arteriosclerosis, Thrombosis, and Vascular Biology* 19, 1004-1013; Lee G. M., et al., 1993, The dynamic structure of the pericellular matrix on living cells, *The Journal of Cell Biology* 123, 1899-1907). The RBCs are used as "particles" and added to the sample to see if/when they are excluded from the cell surface in order to visualize the historically difficult-to-label HA-rich cell coat. Applicants have improved this technique by introducing passivated nanoparticles for the exclusion assay, and doing size-dependent studies that look at which sizes are held at the edge of the PCM and which penetrate.

Figure 27:
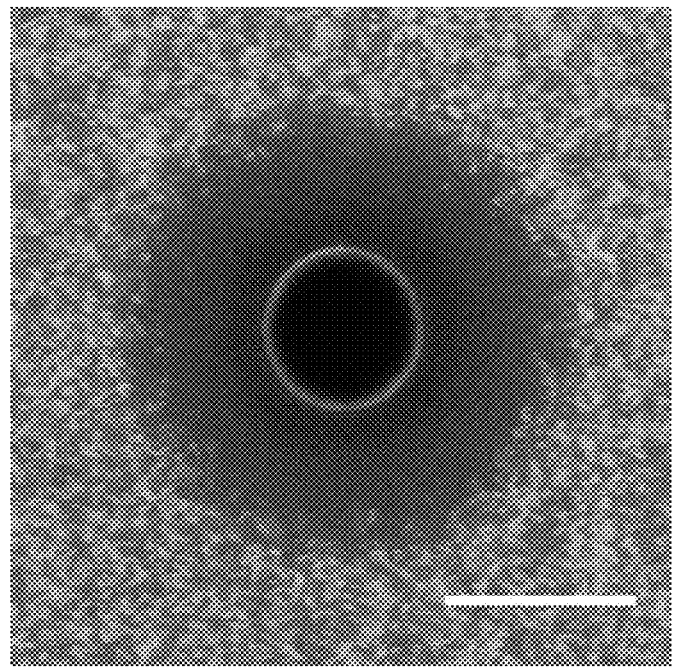
FIG. 27 shows a particle exclusion assay using 200 nm polystyrene passivated with PEG (particles are shown in red) and dextran (10 kDa; shown in green) showing a small gradient towards bead surface (scale bar is 10 μm).

Applicants have discovered that polymer brushes generated by HA synthase membrane fragments, exclude 200 nm particles at all conditions tested. FIG. 27 shows a particle exclusion assay using 200 nm polystyrene passivated with PEG (particles are shown in red) and dextran (10 kDa; shown in green) showing a small gradient towards bead surface (scale bar in figure is 10 µm). In low ionic strength conditions (1 mM), the brush stretched to an average of 7.6 µm. Under high ionic strength conditions (125 mM) the brush extension was over 3 µm.

Figure 28:
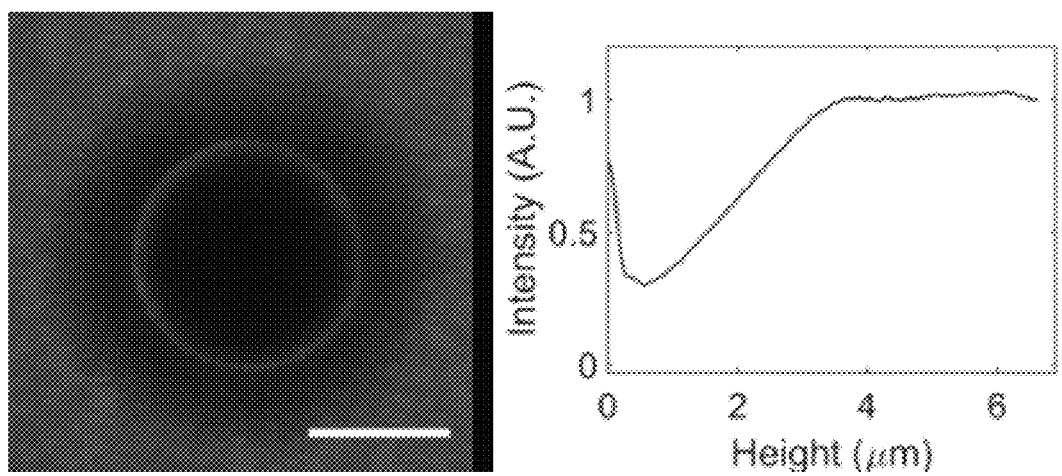
FIG. 28 illustrates the distribution of passivated particles (20 nm) that penetrate into a HA brush (4-hour growth period on an 8 μm sphere). The average azimuthal intensity profile (left) reveals a gradient in bead concentration.

The distribution of twenty passivated particles (20 nm) that penetrate into a HA brush (4-hour growth period on an 8 µm sphere) is shown in FIG. 28. As illustrated, particles filter through the brush in a size-dependent fashion, only allowing certain sizes to reach the solid interface. Further, the distributions throughout the brush depend strongly on particle size. The average azimuthal intensity profile (FIG. 28, left) reveals a gradient in bead concentration.

Example 28

Binding of Histones to HA Polymers

Figure 29:
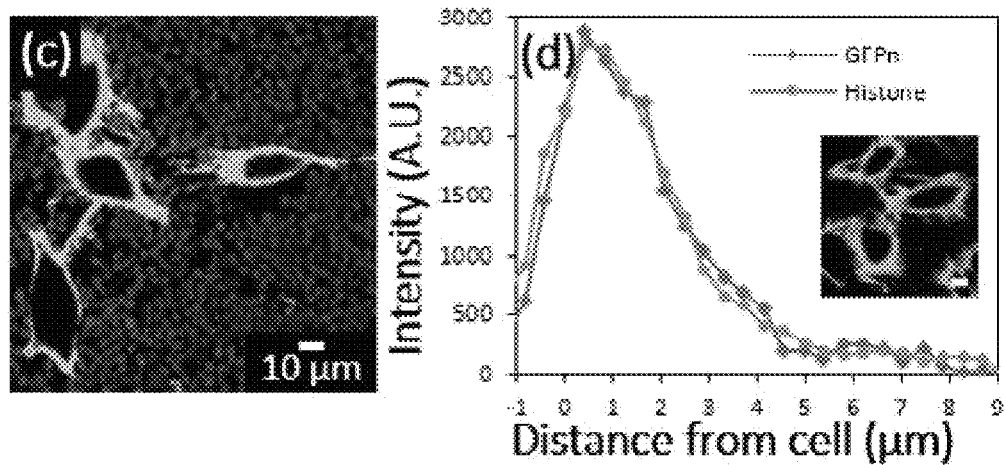
FIG. 29 shows chondrocyte cells with 5 μm thick HA-rich pericellular matrix absorbing fluorescent histone proteins (blue) on bottlebrush proteoglycans. The red particles (left image) are fixed red blood cells, typically used in pericellular matrix studies for particle exclusion assays. Hyaluronan profile (GFPn) is identical to histone profile perpendicular to the cell surface (right image).

This examples describes an experiment examining the binding of positively-charged fluorescent histones (a model surrogate for growth factors) to negatively charged bottle-brush proteoglycans distributed along the HA polymers. As shown in FIG. 29 (left), chondrocyte cells with 5 µm thick HA-rich pericellular matrix absorb fluorescent histone proteins (blue) on bottlebrush proteoglycans. The red particles in FIG. 29 (left) are fixed red blood cells, typically used in pericellular matrix studies for particle exclusion assays. Hyaluronan profile (GFPn) is identical to histone profile perpendicular to the cell surface (FIG. 29, right).

Example 29

Characterizing HA Polymer Brush Height Over Time

Figure 30:
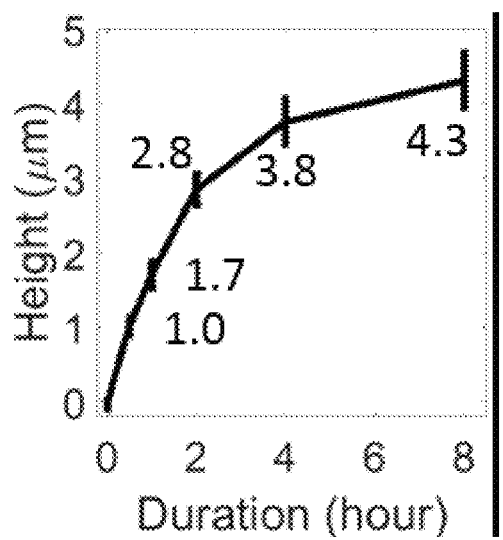
FIG. 30 shows height measurements of an HA synthase brush grown on 8 μm spheres over 8 hours.

This example describes an experiment in which the height of the HA polymer brush was measured over time. Applicants have established several independent and complementary methods to evaluate brush height versus time. Analysis of GFPn profiles to find height provides values in agreement with measurement using particle exclusion assays of the same sample (200 nm passivated particles). For example, the height of a HAS brush grown on 8 micron spheres after 8 hours was found to be 4.31±0.36 µm (for N=205 particles at 125 mM, 7.3 pH) in a particle exclusion assay using 200 nm PEGylated particles (FIG. 30).

Example 30

Interferometric Approach for Characterizing HA Polymer Brush Thickness

This example describes a high throughput interferometric approach to determine the evolution of HA brush thickness. While the particle exclusion assays and fluorescent GFPn are effective, they require taking z-stacks of the HA synthase particles and then carefully identifying the center of the particle and extracting the brush thickness to achieve ~100 nm accuracy. This process is labor intensive, time consuming, and limiting in the number of experiments that can be performed. Further, for some applications, especially studies of brush growth or aging, it is advantageous to follow the same interfaces (particles or location on a planar interface) over time. This is not easily done when adding and taking away reagents like GFPn or when a person must sit at the microscope for the duration of the experiment for extended hours.

Figure 31:
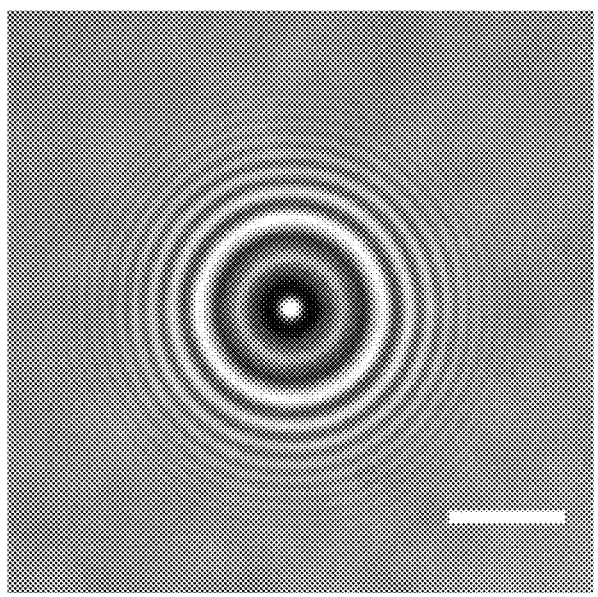
FIG. 31 shows a diffraction pattern of an 8 μm sphere.

With the interferometric approach, the diffraction ring pattern of the glass bead under collimated illumination is monitored over time. (De Vlaminck I et al., 2011, Highly parallel magnetic tweezers by targeted DNA tethering, *Nano Letters* 11, 5489-5493; Dulin D. et al., 2015, High Spatiotemporal-Resolution Magnetic Tweezers: Calibration and Applications for DNA Dynamics, *Biophysical Journal* 109, 2113-2125; Huhle, A. et al., 2015, Camera-based three-dimensional real-time particle tracking at kHz rates and Angstrom accuracy, *Nature communications* 6, 5885-5885; Lansdorp B. M., et al., 2013, A high-speed magnetic tweezer beyond 10,000 frames per second, *Review of Scientific Instruments* 84, 044301). Changes in the pattern can be used to locate bead height with at least ~10 nm resolution. Calibration of bead height is achieved by building a z stack image library by precisely changing the height of the piezo stage and recording the ring pattern for bead attached to the surface. With that library, the dynamic images collected of beads as they change distance to the surface due to HA growth can be analyzed. The tracking accuracy is limited by the piezo used to build the library and has demonstrated to reach the Angstrom-level (Lansdorp B. M., et al., 2013, A high-speed magnetic tweezer beyond 10,000 frames per second, *Review of Scientific Instruments* 84, 044301). Reference beads fixed to the surface are used to track focus drift. A feedback loop to adjust for drift is available. As a result, tracking of bead height and x-y position can be realized over days. Coupled with a programmable stage, Applicants estimate we can track 200 particles simultaneously over days. The diffraction pattern of an 8 µm sphere is shown in FIG. 31 (scale is 10 µm).

Example 31

Characterization of HA Molecular Mass Distribution

This example describes methods for the quantification and characterization of HA production. A summary of methods to quantify the HA production by HA synthase is shown in Table 2.

TABLE 2

Methods to Quantify HA Production.

| Characterization Equipment | Minimum Volume | Minimum Concentration | Property |
|---|---|---|---|
| ELISA | 50 µL | 0.6 ng/mL | Mass concentration of HA (Mw > 35 kDa) |
| CTAB Turbidimetric | 50 µL | 1.5 µg/mL | Mass concentration |
| Carbazole | 50 µL | 4 µg/mL | Mass concentration |
| Dynamic Light Scattering | 50 µL | 2 mg/mL (at 14 kDa) | Estimate of average hydrodynamic radius |
| SEC-MALLS | 500 µL | 10 µg/mL (at 1 MDa) | Accurate molecular mass (length) distribution |

Methods of use involving size-exclusion chromatography coupled to multi-angled light scattering (SEC-MALS) for determining the full length distribution of HA generated by HA synthase can be carried out as described previously (Weigel P. H., et al., 2012, Hyaluronan synthase polymerizing activity and control of product size are discrete enzyme functions that can be uncoupled by mutagenesis of conserved cysteines, Glycobiology 22, 1302-1310; Baggenstoss B. A., et al., 2006, Size exclusion chromatography-multiangle laser light scattering analysis of hyaluronan size distributions made by membrane-bound hyaluronan synthase, *Analytical biochemistry* 352, 243-251). Samples from multiple experiments are batched processed to reach the volumes and concentrations needed for light scattering and SEC-MALS. About 5-10 µg sample is believed to be needed to acquire SEC-MALS data.

Example 32

Characterization of HA Polymer Brush by Microfluidics

This example describes a method of HA characterization using microfluidics. In general, it is difficult to characterize HA systems that generate small amounts of HA, as well as very long HA molecules that are difficult to properly characterize in size assays (Luan T. et al., 2011, Compared molecular characterization of hyaluronan using multiple-detection techniques, *Polymer* 52, 5648-5658). However, Applicants have found that microfluidics and fluorescence microscopy are useful techniques to analyze the length distribution of HA molecules. Applicants' method uses fluidics to stretch out the HA via shear flow (Ladoux B. et al., 2000, Stretching tethered DNA chains in shear flow, *EPL (Europhysics Letters)* 52, 511) above a purposely HA-sticky surface (e.g. poly-L-lysine). A small sample is flowed through microfluidics, designed to force HA to stretch and stick to the surface. Then the HA can be fluorescently labeled using GFP-link neurocan. Finally, automated microscopy and image analysis is used to identify and quantify the length of the HA strands. This process facilitates measurement of the HA length distribution using smaller amounts of sample.

Example 33

Microdialysis Chambers for Solvent Exchange and Reagent Delivery

Figure 32:
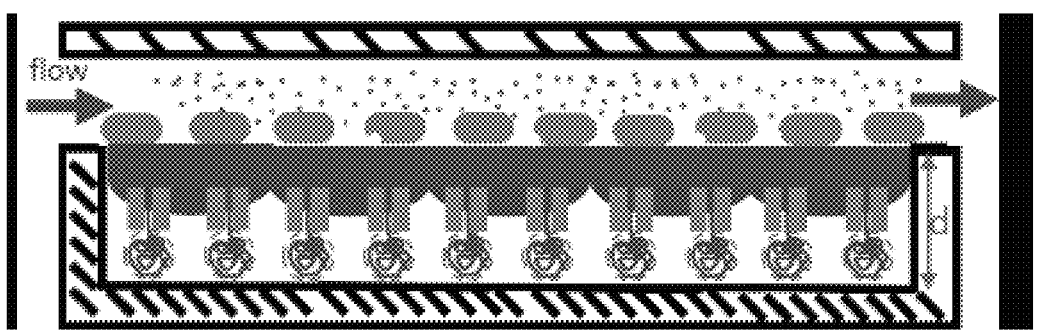
FIG. 32, shows an illustration of microfabricated wells integrated with dialysis membrane that can be used to study confined HA synthase brushes.

A method of integrating a dialysis membrane with microchambers and fluidics in order to facilitate mass transport and exchange of small reagents while confining proteins and polymers and minimizing flow was described previously (Scrimgeour J. et al, 2011, Microfluidic dialysis cell for characterization of macromolecule interactions, *Soft Matter* 7, 4762-4767). The same approach can be used to ensure that HA synthase function is not diffusion limited and that fluid flow used for replenishment does not impact HA synthase function. Further, this scheme can be used to deliver necessary reagents for HA synthase activity (sugars, $Mg^{2+}$) from within a capsule (or implant) rather than relying on an external supply above the interface. This enables the potential to use dynamic HA synthase interfaces in vivo and to use them repeatedly. As shown in FIG. 32, microfabricated wells integrated with dialysis membrane can be used to study confined HA synthase brushes (height, d, will vary). The lower region also can be opened to allow flow and removal for analysis Example 34

Brush Structure in Relation to Solvent and Substrate Properties

Since the pioneering work by de Gennes (de Gennes P G, 1987, Polymers at an interface; a simplified view, *Advances in Colloid and Interface Science* 27, 189-209) on the structure of homodisperse polymer brushes, numerous theoretical, computational and experimental works have achieved a good understanding of the structure of brushes with monodisperse polymers. However, few theoretical studies have focused on polymer brushes comprised of polydisperse polymers (de Vos W. M., et al., 2009, Modeling the structure of a polydisperse polymer brush, *Polymer* 50, 305-316; Milner S. T., et al., 1989, Effects of polydispersity in the end-grafted polymer brush, *Macromolecules* 22, 853-861). There are even fewer experimental studies on polydisperse brushes, most of which we summarize here. There are neutron reflectivity experiments on bi-disperse brushes (Kent M. S. et al., 1996, Structure of Bimodal Polymer Brushes in a Good Solvent by Neutron Reflectivity, *Macromolecules* 29, 2843-2849; Currie E. P. K., et al., 1999, Grafted Adsorbing Polymers: Scaling Behavior and Phase Transitions, *Macromolecules* 32, 487-498) and tri-disperse brushes, (Kritikos G. et al., 2005, Structure of bimodal and polydisperse polymer brushes in a good solvent studied by numerical mean field theory, *Polymer* 46, 8355-8365) and a few studies on polydisperse brushes using the surface force apparatus (Ruths M. et al., 2000, Repulsive Forces and Relaxation on Compression of Entangled, Polydisperse Polystyrene Brushes, *Macromolecules* 33, 3860-3870; Liao W-P, et al., 2013, Normal and shear interactions between high grafting density polymer brushes grown by atom transfer radical polymerization, *Soft Matter* 9, 5753-5761; Dunlop I. E., et al., 2009, Direct Measurement of Normal and Shear Forces between Surface-Grown Polyelectrolyte Layers, *The Journal of Physical Chemistry B* 113, 3947-3956). Thus, the insights gained here, by systematically characterizing the polymer brush concentration profile, thickness and interaction with particles, proteins versus a variety of substrate and solvent changes is of great value.

A. Varying Grafting Density Via HA Synthase Expression Levels:

Polymer brush properties including concentration profile, thickness and ability to filter particles depend on the grafting density of the polymer at the surface. This experiment describes a method to compare the range of grafting densities available to this system by varying HA synthase expression in the bacterial membranes and characterizing the resultant impact on the polymer brush features.

For both monodisperse and polydisperse polymer brushes, the brush height scales with the grafting density, $\sigma$, as: $h \sim \sigma^{1/3}$. The concentration profile for a monodisperse brush is the classic Milner-Witten-Cates prediction of a parabolic distribution. But as our data shows, the high polydispersity of the HA from HA synthase leads to a more exponentially decaying profile, consistent with theory recently published by de Vos and Leermakers (de Vos W. M., et al., 2009, Modeling the structure of a polydisperse polymer brush, *Polymer* 50, 305-316).

The HA synthase density in bacteria can be varied using two different constructs. The first is the pk233 vector, which with induction provides the highest possible HAS gene expression that the Applicant could realize. The second vector called pBAD allows variable production of HA synthase. With low levels of induction, pBAD generates 1% of the HA synthase density generated by the pk233. Higher levels of induction allow higher levels of HAS expression. The relative amount of active HA synthase expression levels in the membrane can be characterized to estimate the relative HA grafting density. To do this, the total HA mass produced by fragments with different HAS expression levels can be compared using the carbazole assay (see Table 1).

HA brush characteristics for several HA synthase densities (and hence grafting densities) can be explored, including the maximum from the pK233 vector for which the HAS separation is estimated to be ~20 nm; the lowest expression level possible (s~200 nm), and at minimum, one intermediate value.

B. Ionic Strength and pH

Hyaluronan is an anionic polymer whose charge impacts the structure of the polymer brush; this is most clearly apparent when comparing the brush thickness of the same particle at high ionic strength (125 mM) and low ionic strength (10 mM). Low ionic strength leads to reduced electrostatic screening and significant repulsion and stretching of the HA polymers. The average brush height increases from 3.75±0.30 μm (N=146) to 7.64±0.42 μm (N=68). Similarly, since each disaccharide carries a carboxyl group, altering the pH impacts the charge state of hyaluronan. At pH below 4, HA has been shown to crosslink and gel (Gatej I. et al., 2005, Role of the pH on Hyaluronan Behavior in Aqueous Solution, *Biomacromolecules* 6, 61-67; Isayeva I. et al., 2010, pH effect on the synthesis, shear properties, and homogeneity of iron-crosslinked hyaluronic acid-based gel/adhesion barrier, *Journal of Biomedical Materials Research Part B: Applied Biomaterials* 95B, 9-18). This significantly alters the HA synthase brush state.

HA synthesis and polymer brush formation can be run under normal conditions until the equilibrium length is reached. Then the solution can be gently exchanged to alter the environmental conditions. Low and high ionic strengths, a range of pH values, solvent quality, and as well as the impact of divalent ions on brush structure ($CaCl_2$ since it is common in tissues) can be measured. GFPn and interferometric microscopy can be used to monitor the dynamic changes of the brush as it stretches or collapses. The final equilibrium brush configuration can be characterized, including height, HA concentration profile, and interaction with nanoparticles and proteins. Measured properties can be compared with theoretical predictions. (Attili S. et al., 2012, Films of End-Grafted Hyaluronan Are a Prototype of a Brush of a Strongly Charged, Semiflexible Polyelectrolyte with Intrinsic Excluded Volume, *Biomacromolecules* 13, 1466-1477; de Vos W. M., et al., 2009, Modeling the structure of a polydisperse polymer brush, *Polymer* 50, 305-316; Milner S. T., 1991, Polymer brushes, *Science* (New York, N.Y.) 251, 905-914; Wijmans C. M., et al., 1993, Polymer brushes at curved surfaces, *Macromolecules* 26, 7214-7224)

C. Substrate Curvature

The configuration and density profile of a polymer brush depends on the curvature of the underlying substrate. Since some HA brush applications use flat surfaces and others, like drug delivery, require highly curved surfaces, it is important to characterize the brush properties of flat interfaces versus curved particles whose radii place them in the two classic regimes: the first is where curvature dominates the brush structure; and second, an intermediate curvature regime where there is a crossover in the brush configuration in the middle of the brush from being dominated by curvature (near the surface) and more like a brush on a flat interface at further distances.

Figure 33:
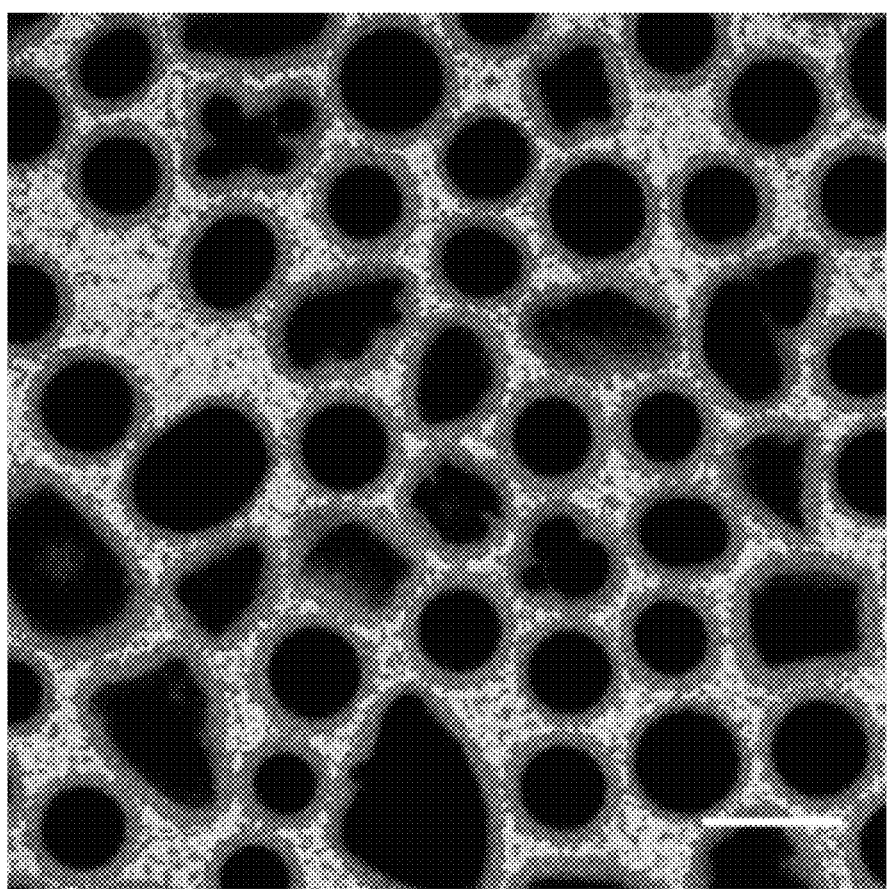
FIG. 33 shows HA synthase fragments grown on interfaces of curvatures to generate microns thick polymer brushes. Brush is formed after two hours incubation; green indicates brush area (green is dextran), red particles (200 nm), overlap appears yellow. Scale bar shown is 20 μm.

Applicants have demonstrated that HAS fragments can be attached and HA brushes grown on a variety of curved surfaces, both uniform and non-uniform. As shown in FIG. 33 (scale bar shown is 20 μm), HA synthase fragments can be grown on interfaces of all curvatures to generate microns thick polymer brushes. FIG. 33 illustrates brush formed after two hours incubation; green indicates brush area (green is dextran), red particles (200 nm), overlap appears yellow). The same technology is easily transferred to planar substrates. Brush structures on particles with a radius of 10 μm, 5, 3, and 1 μm, and on a planar substrate can be analyzed using this method. In each case, SEM analysis can be used to ensure optimal coverage of the surface by bacterial HAS fragments.

Example 35

Molecular Mass Distribution of HA Synthase Brushes

A full analysis and comparison with theoretical predictions of the polymer brush characteristics requires detailed information regarding the length distribution (molecular mass) of the hyaluronan. Applicants have discovered that HA synthases produces a broad distribution of HA lengths. Under normal measurement conditions, which includes extensive vibration during HA growth, the typical distribution can span 0.5-4.0 MDa (1.25-10 µm) under certain conditions. Applicants have discovered that changes in fragment concentration in solution changes the final distribution, where more dilute suspensions produce longer HA chains. It is believed that HA synthase activity and final HA distribution can depend on the grafting density (HAS expression level), the fragment density on the substrate, and the curvature of the substrate. Further, growth in the quiescent conditions of the fluidic chambers can lead to differences as well (versus constant mechanical vibration).

The length distributions for these different scenarios can be determined using SEC-MALS following using published protocols to characterize high molecular weight HA distributions. At specified times, the HA synthase can be quenched (e.g., remove Mg' and sugar substrates, increase EDTA). Then HA can be gently removed from the HA synthase using SDS and flow in chambers with planar substrates. For HA on glass beads, the HAS beads are allowed to sink through a column. Then the supernatant is removed, SDS added, and the column is flipped. The HA desorbs and still in the liquid while the beads sink to the bottom. The collected HA solution is then run through SEC-MALS. HA stores well and does not deteriorate over a few months of storage.

Example 36

Aging of HA Synthase Brush Interfaces

In general, hyaluronan only remains temporarily bound to HA synthase. Knowing the release rate of HA from HA synthase (including HA synthase in dense grafting states) is important for several reasons. First, one can predict the aging and evolution of HA synthase polymer brushes over time. Second, the ability to program HA synthase to produce certain distributions and the ability to adjust the release rates (by genetic engineering of HAS) is very useful in biomaterials applications.

Figure 34:
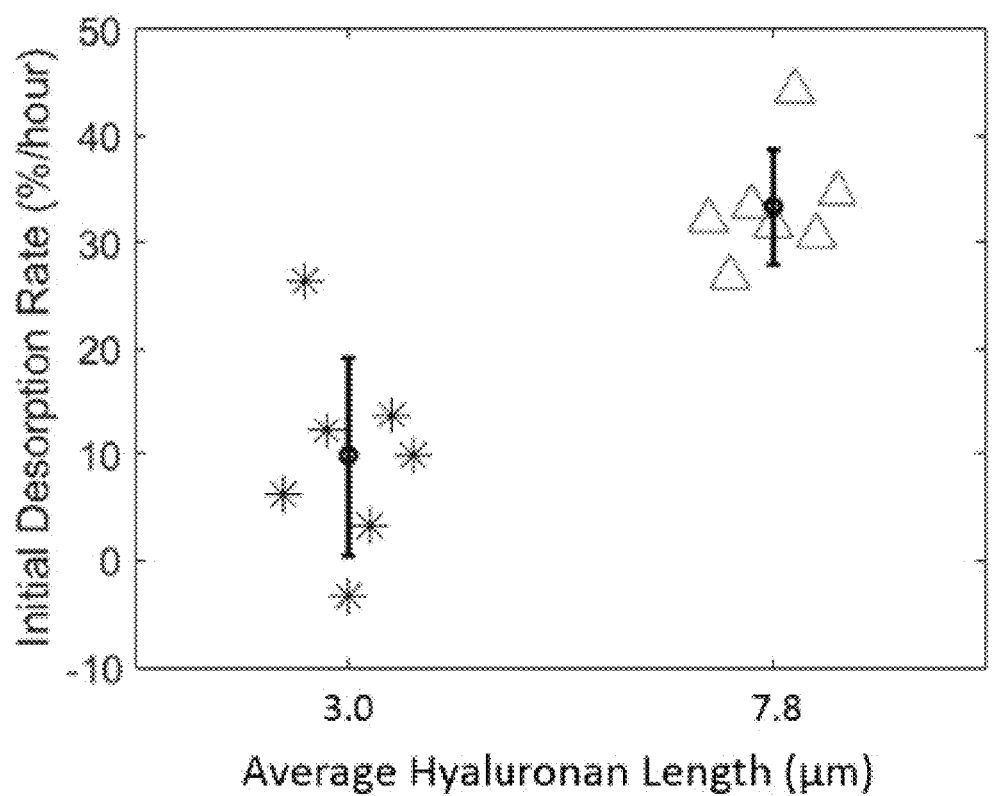
FIG. 34 illustrates the release kinetics of hyaluronan from HA synthase interfaces (8 μm spheres).

Applicants' biophysical analysis of broad HA mass distribution suggest an unexpected length-dependent release of HA from HAS, with longer strands releasing more quickly (Weigel P. H., et al., 2012, Hyaluronan synthase polymerizing activity and control of product size are discrete enzyme functions that can be uncoupled by mutagenesis of conserved cysteines, Glycobiology 22, 1302-1310.; Kumari K., et al., 2006, Mutation of two intramembrane polar residues conserved within the hyaluronan synthase family alters hyaluronan product size, *Journal of Biological Chemistry* 281, 11755-11760.; Weigel P. H., et al., 2002, Functional characteristics and catalytic mechanisms of the bacterial hyaluronan synthases, *Iubmb Life* 54, 201-211). For example, as shown in FIG. 34, release kinetics of hyaluronan from HA synthase interfaces (8 µm spheres) depends on the polymer length. For an average length estimated ~7.8 µm, the desorption rate is approximately 3× faster than for shorter 3 µm HA strands. The same type of analysis can also be used to look at the decay of HA brush thickness versus time, both of flat interfaces and particles. These results are important for providing insight into HA brush performance over time. Further, detailed understanding of the time dependent release of HA versus the average brush thickness is relevant for applications that may require local delivery of HA and slow release of HA over time, such as in wound healing, brain repair and cancer therapies. Interferometric microscopy can be used to measure with nanoscale resolution (~10 nm) how the brush thickness changes with time as HA detaches from HA synthase.

Example 37

Reinforced Covalent Attachment of HA Brush

Some useful applications of the invention require dynamic HA interfaces, where HA synthesis can be turned on in situ. Other applications require permanently bound HA polymer brushes.

In order to achieve permanent robustly bound HA brush, Applicants developed a protocol to covalently bond the HA to the fragments/HA synthase and have shown that the HA remains bound stably for more than a month. The stability of natural HA synthase brush interfaces compared to reinforced HA brush interfaces is shown in FIG. 35 (a 4 hour synthesis was used). Particle exclusion assay analysis shows that the brush thickness after chemical bonding is slightly decreased from ~3.8 µm (N=146, 4 hour synthesis) to ~2.7 µm (N=100), but after that, the thickness is near constant. Indeed, at 2½ months (by eye, not fully quantified) showed that the particles still retain HA brush >2 microns.

Further, HA brushes can be prepared and reinforced by chemical binding using EDC-NHS chemistry. Specifically, after HA synthesis, the substrate was washed 5 times with 75 mM NaKPO$_4$, pH 7.0, 50 mM NaCl. It was then immersed in 100 mM EDC, 40 mM sulfo-NHS. The EDC-NHS buffer was exchanged every 30 minutes three times to ensure activity of the EDC when it diffuses through the HA to the bead surface (because it can also react with the HA). Then the beads were left in room temperature overnight in the EDC-NHS, after which the substrate was washed 3 times with 50 mM borate buffer pH 8.6 and incubated for 2 hours to promote hydrolysis of the NHS esters. In a final step, the reinforced polymer brush interface was washed 5 times with 75 mM NaKPO$_4$, pH 7.3, 50 mM NaCl. The carboxyl groups of the HA can be cross-linked to the amine groups available on the exposed PEI surface and bacterial membrane fragments in various proteins. The final result is believed to be a non-end grafted HA brush, as portions of the HA can bind anywhere on the substrate.

Example 38

Azide-Modified HA Brush

Azide-modified polymer brushes can be prepared by exchanging the storage buffer of the membrane fragment suspension prepared in Example 1 with activation buffer (pH 7.3, 75 mM NaKPO$_4$, 50 mM NaCl, 20 mM MgCl$_2$, 0.1 mM EDTA). After warming the sample for 45 min in a 30° C. incubator, uridine 5-diphosphoglucuronic acid trisodium salt (UDP-GlcUA, Sigma-Aldrich U6751), 5-diphospho-N-acetylglucosamine sodium salt (UDP-GlcNAc, Sigma-Aldrich) and uridine 5-diphospho-N-azidoacetylglucosamine sodium salt (UDP-GlcNAz) can be added at 0.25 mM to 10 mM. UDP-GlcNAz can be prepared as described previously (Lukose, V. et al., Chemoenzymatic assembly of bacterial glycoconjugates for site-specific orthogonal labeling. Journal of the American Chemical Society, 2015, 137, 12446-12449). HA synthesis can be quenched by exchanging the activation buffer with quenching buffer (pH 7.3, 75 mM NaKPO4, 50 mM NaCl, 20 mM EDTA) via mixing by

Example 39

Suppression of Adhesive Biofilms

Azide-containing HA brushes can be crosslinked by reaction with different amounts of α,ω-dialkynyl-PEG reagents, and tested for adsorption of protein and extracellular polymeric substances (EPS, principally polysaccharides, proteins, teichoic acid, and nucleic acids), comparing to the appropriate controls (natural HA, azide-HA prior to crosslinking). The mechanical properties of the crosslinked brushes can be characterized with AFM. The crosslinking morphology can also be varied. For example, a crosslinked HA layer can be established at the top or bottom of the HA brush by feeding UDP-GlcNAz to the HAS surface only at the beginning or end of the brush growth process. In contrast, uniform crosslinking throughout the HA layer can be accomplished using material made with a constant amount of azide monomer and by allowing the dialkyne to diffuse through the material prior to the addition of soluble and highly diffusible catalyst. These biofilm studies can include three pathogens common in medical infections (*Pseudomonas aeruginosa* PA14, *Staphylococcus aureus* SC01, and *Escherichia coli* ZK2686). Biofilm adhesion can be determined by visually observing whether the bacteria is removed by flow; i.e. the remnant bacteria and possible EPS associated with biofilm on the HA interface can be fluorescently labeled and characterized with confocal microscopy. Remnant bacteria can also be gathered via HYAL digestion of the brush and quantification by determining the number colony forming units (CFU) on agar plate from the sample. Conditions under which biofilms adhere to the HA brush can be identified, and the relative importance of key factors such as brush degradation and substrate rigidity can be determined to design more effective materials.

Example 40

Slow Release of Anti-Microbials to Suppress Bacterial Growth

FIG. 35 illustrates the use of azide-functionalized HA brushes to attach and release antimicrobial compounds, for example, known peptides (Wimley, W. C. Describing the Mechanism of Antimicrobial Peptide Action with the Interfacial Activity Model. ACS Chem. Biol., 2010, 5, 905-917; Glinel, K. et al., Antibacterial surfaces developed from bio-inspired approaches. Acta Biomater., 2012, 8, 1670-1684) over periods of hours to weeks. For this purpose, oxanorbornadiene (OND) technology can be used, which allows control of linker cleavage via retro-Diels-Alder fragmentation over a wide range of rates by changing the substituents on the OND core (68; 69; 70). The combined suppression of biofilm adhesion together with the delivery of anti-microbial compounds can work synergistically to prevent bacterial infection over extended periods.

Example 41

Engineering Surfaces the Repel Bacterial but Enable and/or Prevent Mammalian Cell Adhesion In some applications like implants, interfaces that facilitate mammalian cell adhesion but prevent bacterial growth are beneficial. Therefore, the invention includes methods to design the HA brush interfaces to control both cell and microbe interactions in an optimal fashion. Under conditions of mixed fibroblasts and bacteria, it can be determined whether fibroblasts are able to digest HA and proliferate at the surface while bacterial infection and biofilm adhesion are prevented by the non-fouling and steric repulsion of the brush. Further, the controlled crosslinking of HA brush can be used to prevent HYAL digestion of the HA brush and hence delay or possibly even prevent adhesion of fibroblasts. (Zhong, S. P. et al. Biodegradation of hyaluronic acid derivatives by hyaluronidase. Biomaterials, 1994, 15, 359-365; Mais, V. et al., Reduction of postoperative adhesions with an auto-crosslinked hyaluronan gel in gynaecological laparoscopic surgery: a blinded, controlled, randomized, multicentre study. Human Reproduction, 2006, 21, 1248-1254; De Laco, P. A. et al. A novel hyaluronan-based gel in laparoscopic adhesion prevention: preclinical evaluation in an animal model., 1998, Fertility and Sterility 69, 318-323; Avitabile, T. et al. Biocompatibility and biodegradation of intravitreal hyaluronan implants in rabbits., 2001, Biomaterials 22, 195-200). The click modifications can be systematically varied (slow release of biocide; crosslinking) by tuning the azide-monomer integration into the brush to find optimized conditions.

Example 42

Stability of Azide-Modified Constructs In Vivo

HA brush-coated glass samples made in the above examples can be covalently labeled with a light loading of biocompatible bright dye (Alexa647) by CuAAC attachment, using a noncleavable (short PEG) linker. These test materials can be subcutaneously implanted in CD-1 mice (8-10 weeks of age). Periodic sampling of blood will allow detection of released dye-labeled fragments into circulation over time. In addition, after periods of 1 day to 4 weeks animals can be sacrificed and local tissue and lymph sectioned and assessed for dye distribution. These measurements provide information regarding the stability of the implanted HA materials, reinforced and crosslinked brushes are believed to be the most robust.

Example 43

Inflammatory Response in Vivo

Derivatized HA materials can be examined for biocompatibility by the following experiments. RAW 264.7 macrophages can be cultured in the presence of test materials and the release of pro-inflammatory cytokines IL-1 and TNF-α can be measured for preliminary assessment of inflammatory potential. Standard mouse fibroblast (L-929) (Morais, J. M. et al., Biomaterials/Tissue Interactions: Possible Solutions to Overcome Foreign Body Response, 2010, AAPS J. 12, 188-196) human fibroblast (3T3), and adipocyte (differentiated 3T3-L1) cell lines can also be cultured in the presence of test materials, to determine cell viability and morphology in comparison to control conditions (in vivo). Test materials can be subcutaneously implanted in CD-1 mice (8-10 weeks), with monitoring of animal weight and standard circulating markers of inflammation and immune response (Becton Dickinson CBA mouse kit, covering IL-2, 4, 6, 10, and 17A, interferon-γ, and TNF-α) weekly for four weeks. Serum chemistry panels to monitor liver and renal function can also be performed. Tissue sections at the site of Gently pipetting the liquid up and down. The buffer exchange can be repeated several times.

What is claimed is:

1. A polymer brush comprising:
   a substrate; and
   hyaluronan synthase components attached to about 20 to about 40% of the surface area of the substrate, at least a portion of which being capable of synthesizing a hyaluronic acid having a certain hydrodynamic diameter;
   wherein one or more of the hyaluronan synthase components comprise one or more hyaluronan synthase proteins in a fragment of cell membrane; and
   wherein an average distance between the hyaluronan synthase proteins in the fragment of cell membrane is substantially equal to or less than an average hydrodynamic diameter of the hyaluronic acid.

2. The polymer brush of claim 1, wherein an average distance between the hyaluronan synthase components on the substrate is less than about 1 μm.

3. The polymer brush of claim 1, wherein the fragment of cell membrane comprises bacterial cell membrane.

4. The polymer brush of claim 1, wherein the hyaluronan synthase proteins comprise a *Streptococcus* equisimilus (Group C) hyaluronan synthase.

5. The polymer brush of claim 1, wherein the fragment of cell membrane comprises mammalian cell membrane.

6. The polymer brush of claim 1, wherein the hyaluronic acid is an azide-modified hyaluronic acid.

7. The polymer brush of claim 1, wherein an average height of the polymer brush is in the range of about 500 nm to about 30 μm.

8. The polymer brush of claim 1, wherein an average size of the hyaluronan is less than about 12 MDa.

9. The polymer brush of claim 1, wherein a grafting density of the polymer brush is modified such that it comprises regions comprising inactivated hyaluronan synthase components; and
   wherein the inactivated hyaluronan synthase components are not capable of synthesizing polysaccharide.

10. The polymer brush of claim 1 further comprising hyaluronic acid polymers covalently attached to the substrate at certain grafting points on the substrate.

11. A polymer brush comprising:
    a substrate; and
    hyaluronan synthase components attached to the substrate, at least a portion of which being capable of synthesizing a hyaluronic acid having a certain hydrodynamic diameter;
    wherein one or more of the hyaluronan synthase components comprise one or more hyaluronan synthase proteins in a fragment of cell membrane;
    wherein an average distance between the hyaluronan synthase proteins in the fragment of cell membrane is substantially equal to or less than an average hydrodynamic diameter of the hyaluronic acid; and
    wherein one or more of:
      the hyaluronan synthase components comprise about 20 to about 40% of the surface area of the substrate;
      an average distance between the hyaluronan synthase components on the substrate is less than about 1 μm;
      the hyaluronic acid is an azide-modified hyaluronic acid;
      an average height of the polymer brush is in the range of about 500 nm to about 30 μm;
      an average size of the hyaluronan is less than about 12 MDa; and
      a grafting density of the polymer brush is modified such that it comprises regions comprising inactivated hyaluronan synthase components that are not capable of synthesizing polysaccharide.

12. A method of fabricating the polymer brush of claim 11 comprising applying a solution comprising the hyaluronan synthase components to the substrate such that the hyaluronan synthase components are substantially immobilized on the substrate.

13. The method of claim 12 further comprising treating the substrate with a reaction mixture comprising a nucleotide sugar substrate.

14. The method of claim 13, wherein the nucleotide sugar substrate comprises:
    $MgCl_2$; and
    at least one of:
      uridine 5'-diphosphoglucuronic acid or a salt thereof; and
      uridine 5'-diphospho-N-acetylglucosamine or a salt thereof.

15. The method of claim 13, wherein treating the substrate provides a rapid polymerization.

16. The method of claim 15, further comprising substantially disrupting the rapid polymerization with a treatment of a quenching mixture comprising about 30 mM to about 50 mM EDTA.

17. The method of claim 16 further comprising reinitiating the rapid polymerization by replacing the quenching mixture with a reaction mixture comprising a nucleotide sugar substrate.

18. The method of claim 15, further comprising covalently binding the hyaluronic acid to the substrate to form a reinforced substrate comprising covalently-bound hyaluronic acid polymers.

19. A method of modifying the grafting density of the polymer brush of claim 11 comprising:
    selecting a target region of the polymer brush having the hyaluronan synthase components; and
    irradiating the target region with UV light such that the hyaluronan synthase components in the target region become inactivated;
    wherein the inactivated hyaluronan synthase components are not capable of synthesizing polysaccharide.

* * * * *